(12) United States Patent
Phillips

(10) Patent No.: US 11,020,251 B2
(45) Date of Patent: Jun. 1, 2021

(54) METHODS AND APPARATUS FOR IMPROVED INTERFACE BETWEEN THE HUMAN BODY AND PROSTHETIC OR SIMILAR DEVICES

(71) Applicant: Van L Phillips, Albion, CA (US)

(72) Inventor: Van L Phillips, Albion, CA (US)

(*) Notice: Subject to any disclaimer, the term of this patent is extended or adjusted under 35 U.S.C. 154(b) by 0 days.

(21) Appl. No.: 14/348,401

(22) PCT Filed: Oct. 1, 2012

(86) PCT No.: PCT/US2012/058358
§ 371 (c)(1),
(2) Date: Mar. 28, 2014

(87) PCT Pub. No.: WO2013/049847
PCT Pub. Date: Apr. 4, 2013

(65) Prior Publication Data
US 2014/0288670 A1    Sep. 25, 2014

Related U.S. Application Data

(60) Provisional application No. 61/541,080, filed on Sep. 30, 2011.

(51) Int. Cl.
*A61F 2/78* (2006.01)
*A61F 2/74* (2006.01)
(Continued)

(52) U.S. Cl.
CPC .......... *A61F 2/7843* (2013.01); *A61F 2/7812* (2013.01); *A61F 2002/5027* (2013.01); *A61F 2002/5032* (2013.01); *A61F 2002/704* (2013.01); *A61F 2002/74* (2013.01); *A61F 2002/741* (2013.01); *A61F 2002/745* (2013.01); *A61F 2002/7635* (2013.01); *A61F 2002/7655* (2013.01); *A61F 2002/785* (2013.01)

(58) Field of Classification Search
CPC ........ A61F 2/78; A61F 2/7812; A61F 2/7843; A61F 2/80; A61F 2002/5027; A61F 2002/5032; A61F 2002/5035; A61F 2002/5052; A61F 2002/5083; A61F 2002/6827; A61F 2002/767; A61F 2002/785; A61F 2002/802; A61F 2002/805; A61F 2002/807
See application file for complete search history.

(56) References Cited

U.S. PATENT DOCUMENTS

| 49,234 A | * | 8/1865 | Coombs | A61F 2/78 623/33 |
| 2,594,751 A | * | 4/1952 | Fahlstrom | A61F 2/80 29/426.2 |

(Continued)

*Primary Examiner* — Christie L Bahena
(74) *Attorney, Agent, or Firm* — J. Steven Svoboda

(57) ABSTRACT

Apparatus is provided to cushion between a prosthetic socket and an amputee's residual limb. A plurality of putty-filled packets are assembled into a liner that, when assembled, provides a generally smooth contact surface toward the residual limb. At least one of the packets has a fluid bladder positioned between the putty material and the socket, and the fluid volume in the bladder can be adjusted to affect the fit of the assembly on the residual limb. Methods of fabrication, fitting, and use of such prosthetic devices are disclosed.

1 Claim, 55 Drawing Sheets

(51) Int. Cl.
*A61F 2/76* (2006.01)
*A61F 2/50* (2006.01)
*A61F 2/70* (2006.01)

(56) References Cited

U.S. PATENT DOCUMENTS

| | | | | |
|---|---|---|---|---|
| 3,671,980 | A * | 6/1972 | Baird | A61F 2/80 623/37 |
| 5,156,629 | A * | 10/1992 | Shane | A61F 2/7843 128/DIG. 20 |
| 5,464,443 | A * | 11/1995 | Wilson | A61F 2/7843 623/36 |
| 5,507,834 | A * | 4/1996 | Laghi | A61F 2/80 623/34 |
| 6,149,691 | A * | 11/2000 | Fay | A61F 2/80 623/33 |
| 6,867,253 | B1 * | 3/2005 | Chen | A61C 15/00 524/505 |
| 7,655,049 | B2 | 2/2010 | Phillips | |
| 2001/0020142 | A1 * | 9/2001 | Bird | A61F 5/0111 602/13 |
| 2002/0099450 | A1 * | 7/2002 | Dean | A61F 2/76 623/26 |
| 2002/0173856 | A1 * | 11/2002 | Karason | A61F 2/7843 623/37 |
| 2003/0181990 | A1 * | 9/2003 | Phillips | A61F 2/7843 623/37 |
| 2004/0134500 | A1 * | 7/2004 | Ingimundarson | A61F 5/0113 128/882 |
| 2008/0147204 | A1 * | 6/2008 | Ezenwa | A61F 2/68 623/33 |
| 2009/0271000 | A1 * | 10/2009 | Altobelli | A61F 2/7843 623/37 |
| 2011/0247321 | A1 * | 10/2011 | Streeter | A61F 2/68 60/327 |
| 2013/0103125 | A1 * | 4/2013 | Radspieler | A61F 7/02 607/104 |

* cited by examiner

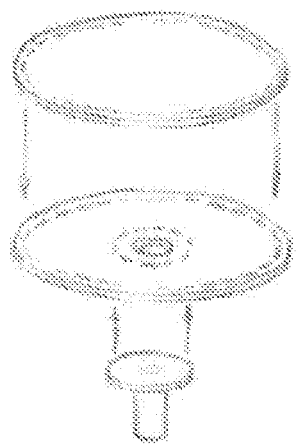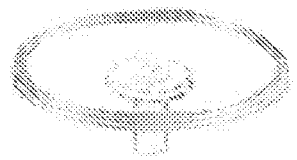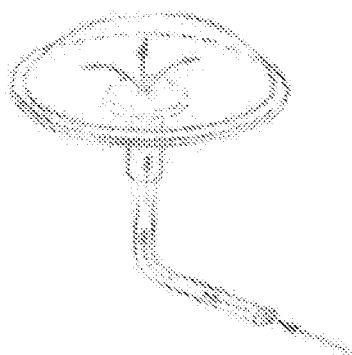
Fig. 9

Fig. 39 - Upper main
Fig. 40 - Lower rung distal
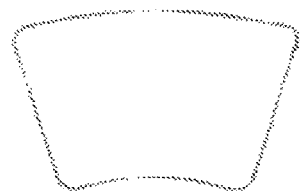
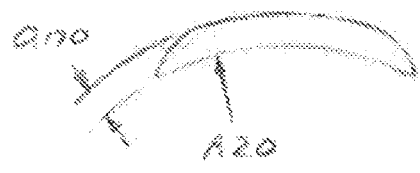
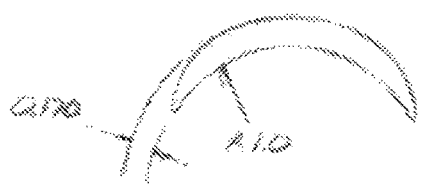
Fig. 41 - Patella
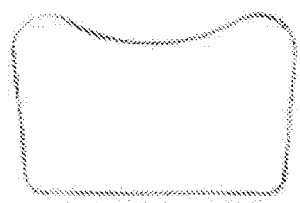
Fig. 42 - Hamstring
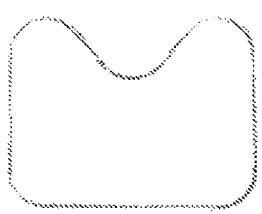

*Fig. 43 - Upper condyle - left*
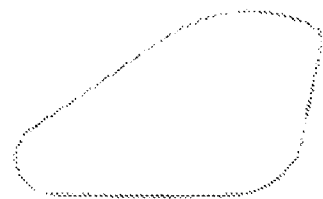
*Fig. 44 - Upper condyle - right*
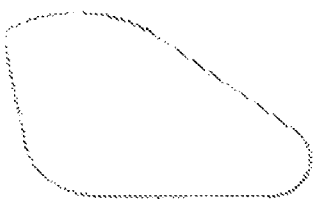
*Fig. 45 - Lower condyle - left*
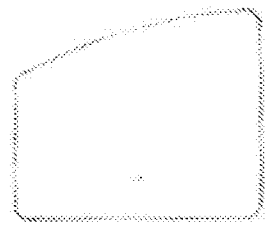
*Fig. 46 - Lower condyle - right*
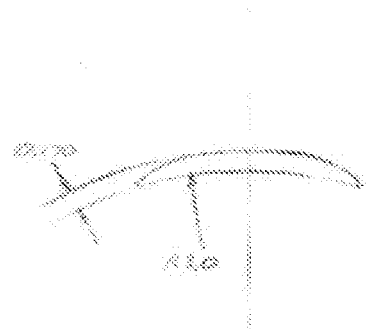

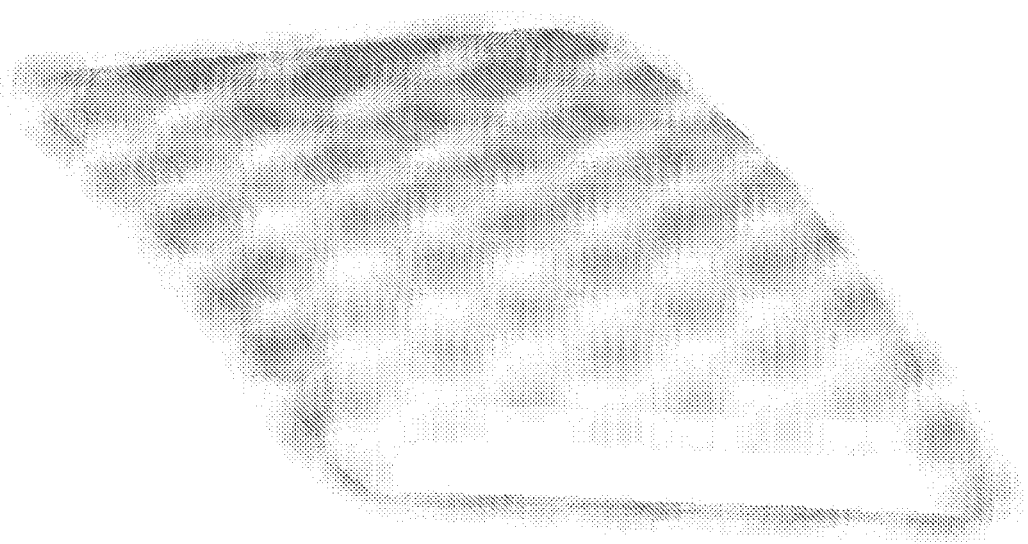
Fig. 48 - Tapered packet - perspective view

METHODS AND APPARATUS FOR IMPROVED INTERFACE BETWEEN THE HUMAN BODY AND PROSTHETIC OR SIMILAR DEVICES

This application is based on and claims the benefits of the filing date of U.S. Provisional Patent Application No. 61/541,080 (filed Sep. 30, 2011).

The present invention is described here with reference to the accompanying Figures, which serve as illustrations of some of the many embodiments in which the invention may be practiced. Generally in those Figures and references (but subject to the context and other factors, including for example the understanding of persons of ordinary skill in the arts relevant to the inventions), similar reference numerals refer to similar or identical elements throughout this description.

Those Figures and references, and the other terminology used in these descriptions, are not intended to be interpreted in any limited or restrictive manner, simply because they are being utilized in conjunction with a detailed description of certain embodiments of the invention. Furthermore, various embodiments of the invention (whether or not specifically described herein) may include one or more novel features, no single one of which (a) is necessarily solely responsible for one or more desirable attributes of the invention or (b) is essential to practicing the inventions described.

DESCRIPTION OF THE DRAWINGS

The accompanying drawings provide visual representations which will be used to more fully describe various representative embodiments and can be used by those skilled in the art to better understand the representative embodiments disclosed herein and their inherent advantages. In these drawings, like reference numerals identify corresponding elements.

FIG. 9 is a set of drawings showing customization of the interface using an inflatable element such as an oil dome.

FIG. 39 is a drawing of an interface with bladder/putty packets that are shaped so that, when assembled within a prosthetic socket, wrinkling, folds, or other deformations are minimized.

FIG. 40 is a drawing of an interface with bladder/putty packets that are shaped so that, when assembled within a prosthetic socket, wrinkling, folds, or other deformations are minimized.

FIG. 41 is a drawing of an interface with bladder/putty packets that are shaped so that, when assembled within a prosthetic socket, wrinkling, folds, or other deformations are minimized.

FIG. 42 is a drawing of an interface with bladder/putty packets that are shaped so that, when assembled within a prosthetic socket, wrinkling, folds, or other deformations are minimized.

FIG. 43 is a drawing of an interface with bladder/putty packets that are shaped so that, when assembled within a prosthetic socket, wrinkling, folds, or other deformations are minimized.

FIG. 44 is a drawing of an interface with bladder/putty packets that are shaped so that, when assembled within a prosthetic socket, wrinkling, folds, or other deformations are minimized.

FIG. 45 is a drawing of an interface with bladder/putty packets that are shaped so that, when assembled within a prosthetic socket, wrinkling, folds, or other deformations are minimized.

FIG. 46 is a drawing of an interface with bladder/putty packets that are shaped so that, when assembled within a prosthetic socket, wrinkling, folds, or other deformations are minimized.

FIG. 48 is a drawing showing a perspective view of an exemplary "custom-curved" bladder/ putty packet usable with an interface.

DETAILED DESCRIPTION

Figure 1:
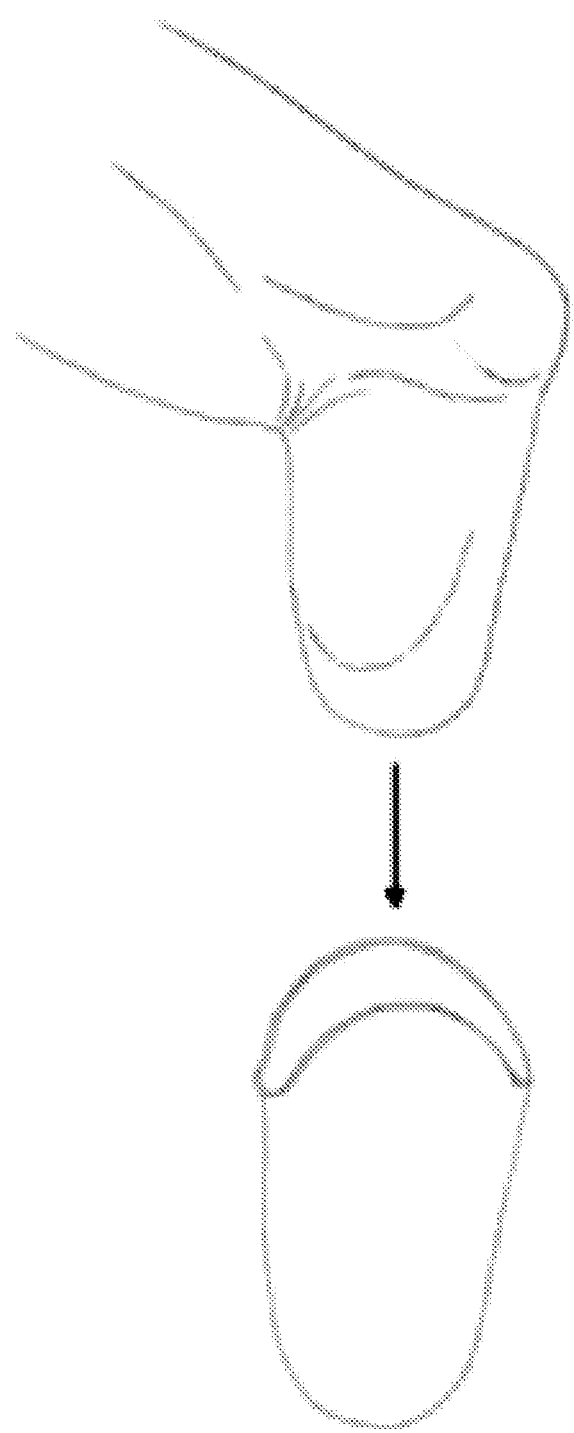
FIG. 1 is a drawing of a lower leg amputee fitted with a socket, and of a contact interface with a prosthetic leg attached to the socket.

As illustrated in FIG. 1, it is common for a lower leg amputee to be fitted with a socket, with a prosthetic leg or other device then attached to that socket. For these and other situations, there is some sort of "contact interface" between a relatively sensitive, fragile, and/or dynamic thing (e.g., the patient's residual limb) and a relatively hard/stiff device (e.g., the prosthetic socket). For example, because lower leg prosthetic devices are load-bearing (the patient's weight is imposed on the socket), the socket or other attachment structure typically requires some relatively "stiff" support structure or elements.

In addition to being hard, the socket/attachment structure commonly is of a relatively fixed configuration. For example, for lower leg amputees, a custom socket is formed to approximate the size and shape of the amputee's residual limb, and the socket element itself does not typically change shape or size.

Although the socket (or other support element) typically is stiff and static in its size and shape, the amputee's residual limb typically is not. Instead, the amputee's residual limb commonly includes muscle and other "soft" tissues, and in fact commonly is dynamic in its size, shape, position, and other characteristics. Among other things, blood flow can affect the size and shape of the residual limb, and the limb can change in size and shape over the course of time.

The present inventions preferably include and/or constitute an improved customizable and/or dynamic interface between an amputee's residual limb and a socket or other prosthetic component. The interface can be assembled in any useful arrangement, including in the form of a sleeve to be placed over the residual limb, fixed to the other component, or others. The apparatus and related methods preferably include a bladder system that, in certain embodiments, can be adjusted to accommodate volume fluctuations in the residual limb, tender areas of the limb, or other special situations.

Preferably, a plurality of bladders are provided, and in one embodiment useful to leg amputees, these bladders are located substantially only between a posterior portion of the limb and the confronting portion of the socket. The components and assemblies of the inventions preferably are simple to fabricate and use and maintain, but more complex embodiments can be utilized in certain circumstances.

The arrangement of the various components can be quite varied, and therefore useful in a wide range of applications, including for a wide range of prosthetic patients. In addition to relatively simple bladders, the inventions include the use of inflatable bladders, and/or separate inflatable/adjustable "oil domes" or similar devices. These various components may be organized into layers, and can utilize multiple and/or intermixed and/or alternating layers of bladders, oil domes, etc. for further fine tuning. Preferably, the inventions lend themselves to providing ready customizable solutions for amputees, as well as for other situations which may benefit from an improved interface between a relatively solid object and a relatively softer and/or fragile object. Among other things, the interface of the inventions herein may find utility in medical splints, interfaces between non-amputated human limbs and other hardware or the like, interfaces between robotic machines and fragile objects that they may need to grasp or manipulate, etc. Other examples include use in ski boots and electronic control "gloves" or other devices (for translating finger and hand movements into digital signals).

The particular materials, dimensions, and fabrication methods for practicing the invention can be selected from a wide range of possibilities, depending on a number of factors (including those discussed in many of my previous patents, which are incorporated herein by reference). Preferably, the inventions are practiced in a modular manner, so that the various components are effectively interchangeable with other such components. Depending on the patient and the application, certain components may need to be shaped slightly differently for cosmetic or other reasons, but their functionality preferably is at least substantially unaffected by such changes.

Figure 2:
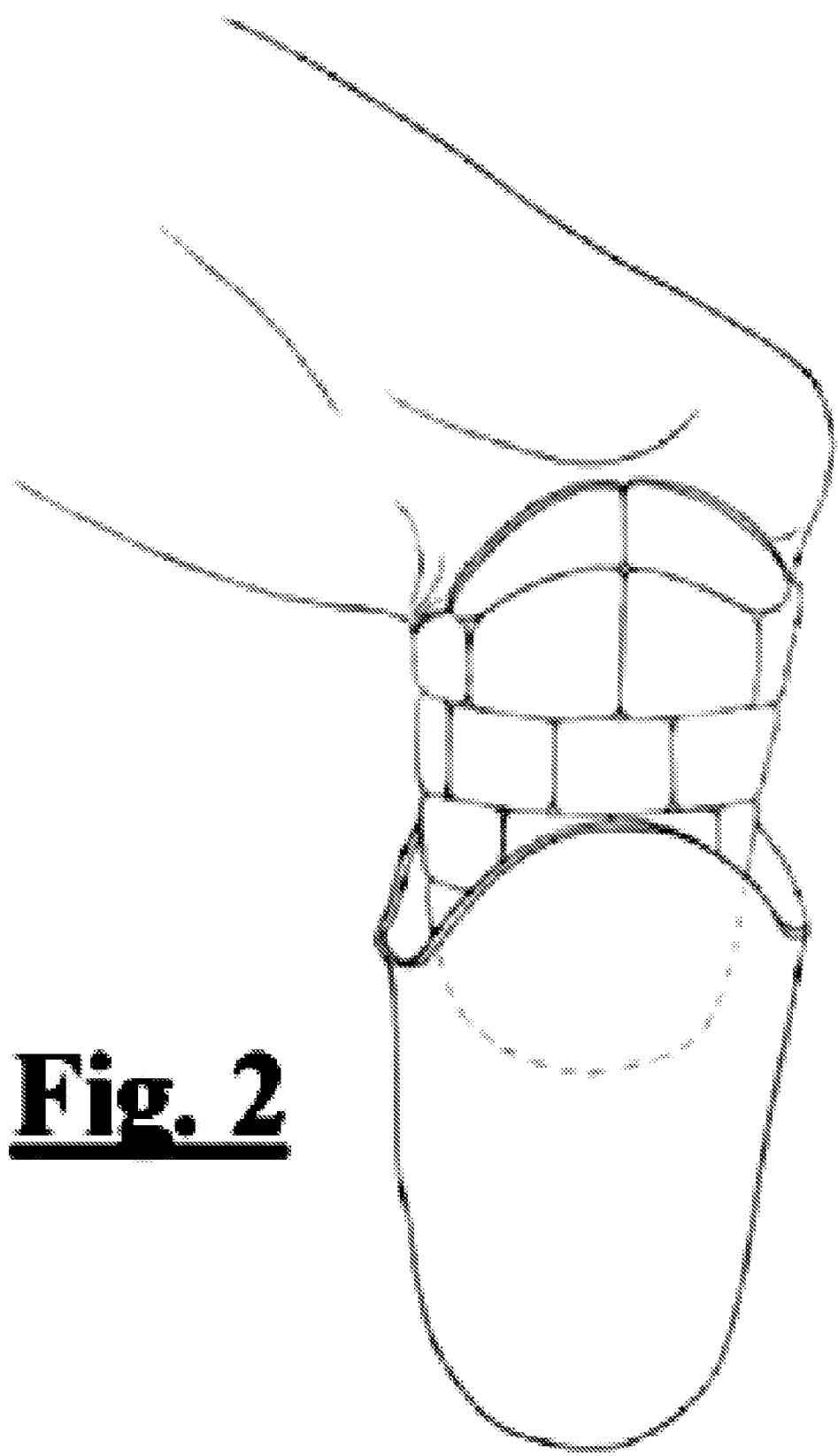
FIG. 2 is a drawing of an interface sleeve positioned between the limb and the socket.
Figure 15:
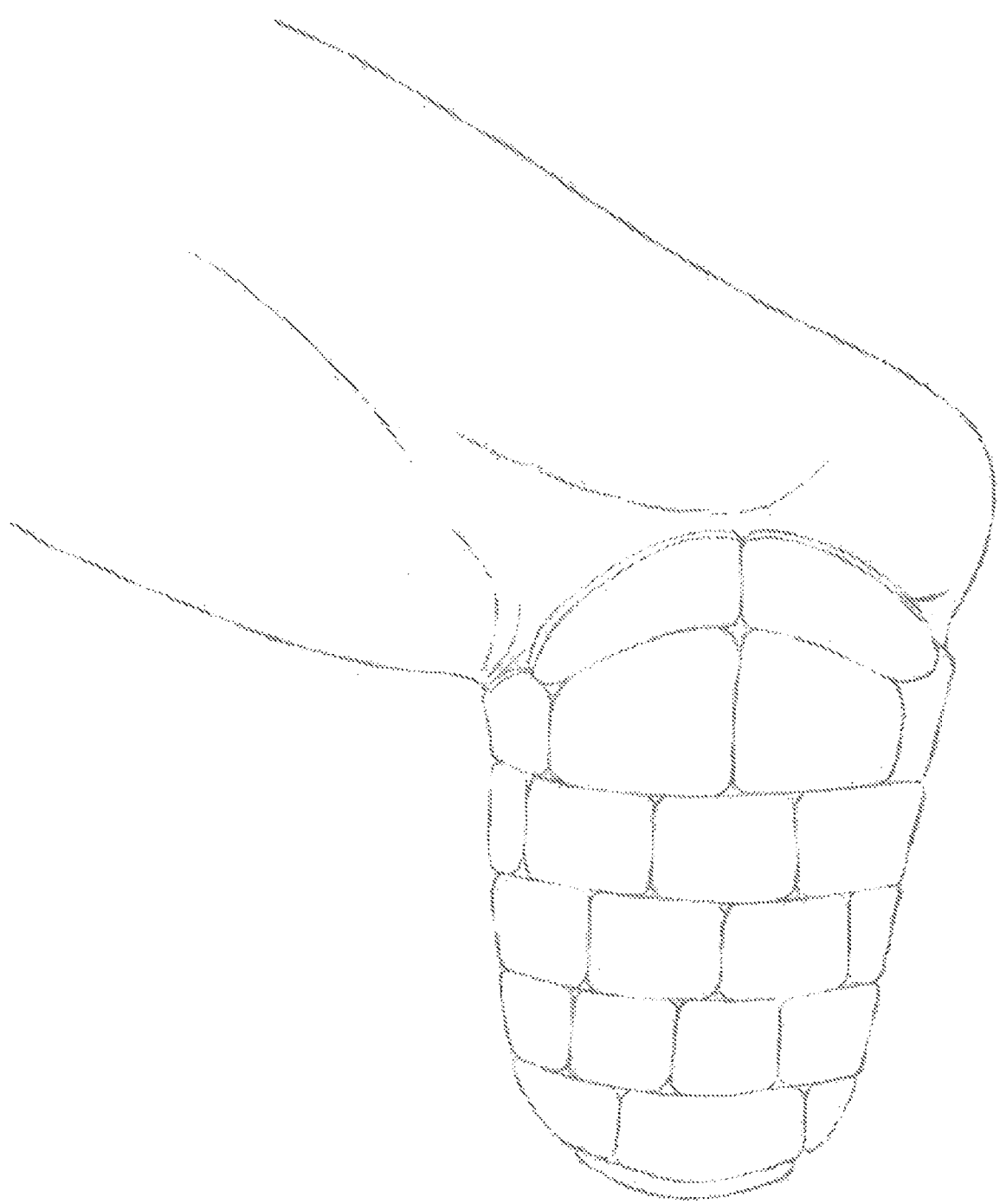
FIG. 15 is a drawing of an interface in which a plurality of bladders are assembled into a sleeve that conforms to the patient's residual limb.

FIGS. 15 and 2 illustrate one of the many embodiments of the invention. As explained below, a plurality of bladders preferably are assembled into a sleeve that conforms to the patient's residual limb (see FIG. 15), and that sleeve is positioned between the limb and the socket (see FIG. 2).

Figure 3:
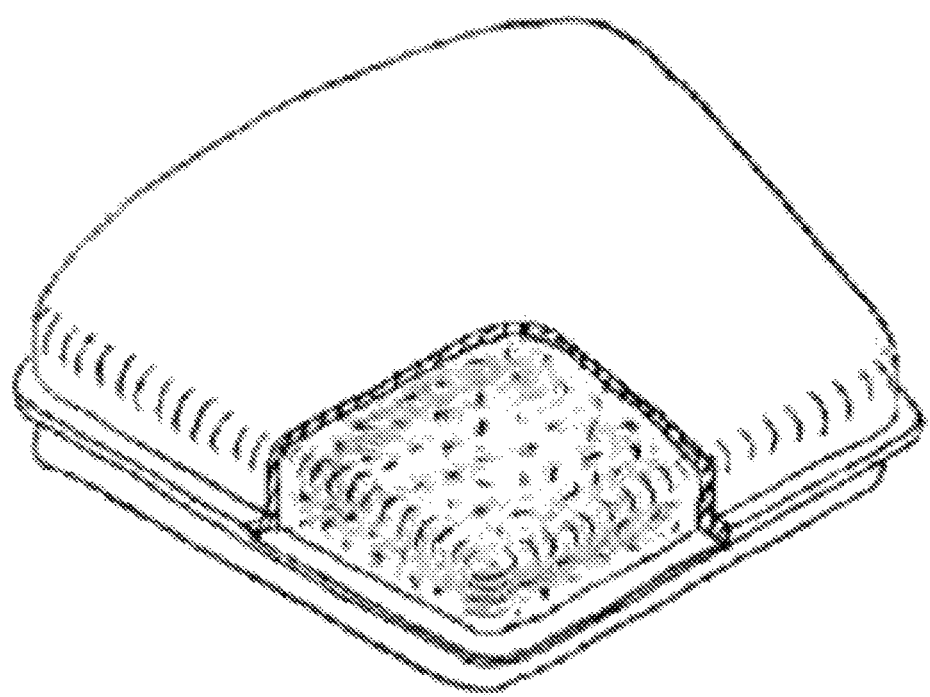
FIG. 3 is a drawing showing a partially cutaway perspective view of fabrication of a bladder usable with the interface.

FIG. 3 is a partially cutaway perspective view that illustrates one of the many ways in which the bladders of the invention may be fabricated. An outer shell preferably is heat sealed at its edges around a viscous material. Among the many useful materials for the shell are polyurethane, vinyl, silicone, and others. Preferably, the shell is thin and flexible, impervious to water and soap and the like, and is tough and durable.

A wide range of suitable viscous materials may be utilized within the bladder. Preferably, the material is a "Non-Newtonian Shear Thickening Fluid" dilatant type, which means that the viscosity increases as the shear rate increases (from force or loading or stress on the material). These materials can be described as having "Shear Rate Thickening" properties, as opposed to the Pseudoplastic type (in which viscosity decreases as shear rate increases, also described as having "Shear Rate Thinning" properties). An example of a suitable viscous material is THERA-PUTTY® resistive hand exercise material, XX-Soft, made by Fabrication Enterprises Incorporated. Persons of ordinary skill in the art will understand that the wide range of other materials that may be used include, without limitation, non-compressible fluids such as FLOAM®, grease, silicone grease, SILLY PUTTY®, ultrapastuerized peanut butter, or the like. Preferably, the material is a solid/liquid/flowable medium, but not a compressible gas. Also preferably, the viscous material is not affected by temperature (meaning that the desired high viscosity will be at least relatively constant), and is non-toxic. For embodiments that use some form of putty, the bladders can be usefully referred to as "putty packets."

In general, less weight is desirable for prosthetic devices. To reduce the weight of each bladder (and thereby the entire prosthetic assembly), preferably plastic beads or spheres (weighing less than an equivalent volume of putty or other material inside the bladder) are mixed into the viscous material. In certain embodiments, the estimated total weight of the liner assembly can be as low as 4 ounces or less. Although any suitable "lightening" material or process may be used, a plastic microsphere material called Expancel, 920 DE80d30, made by AkzoNobel, is suitable. The mix ratio likewise can be any suitable mix, including (by way of example) one part putty to 1.4 parts microspheres, measured by volume. Using that recipe with a putty density of 1.389 g/cm$^3$ and a microsphere density of 0.030 g/cm$^3$, a useful mix density of 0.600 g/cm$^3$ can be achieved.

Figure 4:
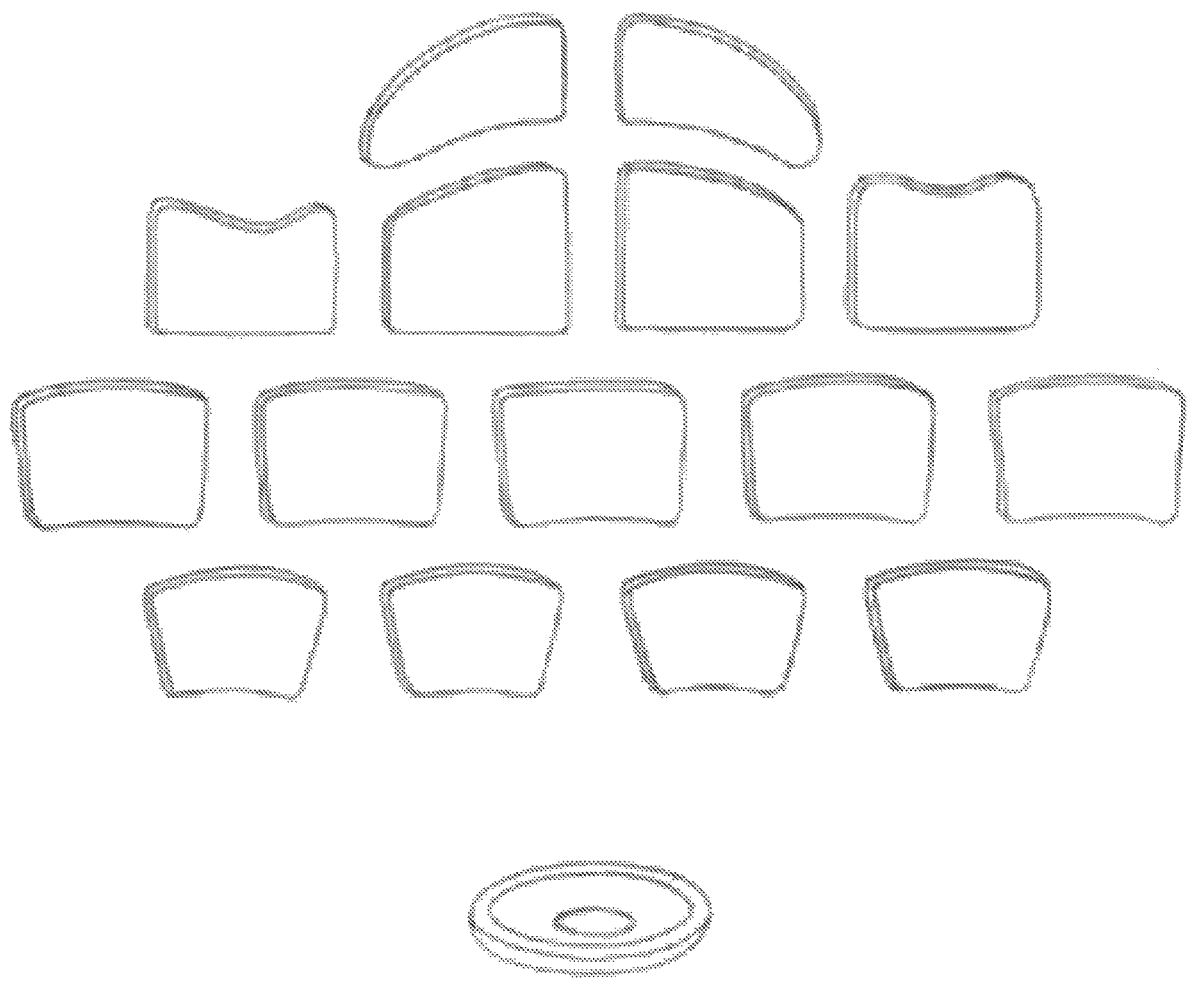
FIG. 4 is a set of drawings of shapes into which bladders usable with the interface can be formed.

FIG. 4 illustrates some of the many shapes into which such bladders or putty packets can be formed. In modular systems, a "standard" set of sizes and shapes can be developed and used to substantial economic and other benefits. Among other things, preferably at least the simpler embodiments of the inventions herein lend themselves to being assembled in the field, in any location in the world, and into a shape that is at least relatively customized to the particular patient or application. Persons of ordinary skill in the art will understand that the bladder shapes are virtually unlimited, the bladders can be jigsawed together in virtually any way; and the number of differently sized/dimensioned/other bladders could be in the tens of thousands or more.

Figure 5:
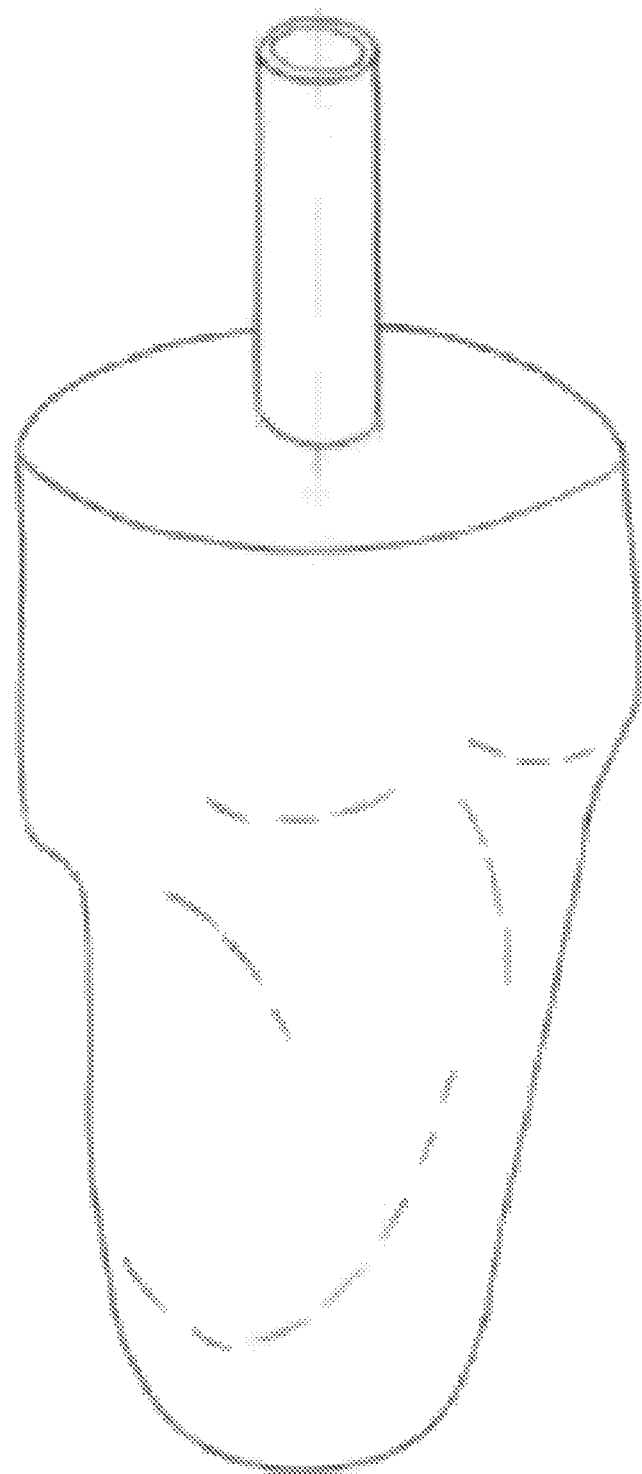
FIG. 5 is a drawing of a plaster cast or model of a limb usable in creating an interface.
Figure 6:
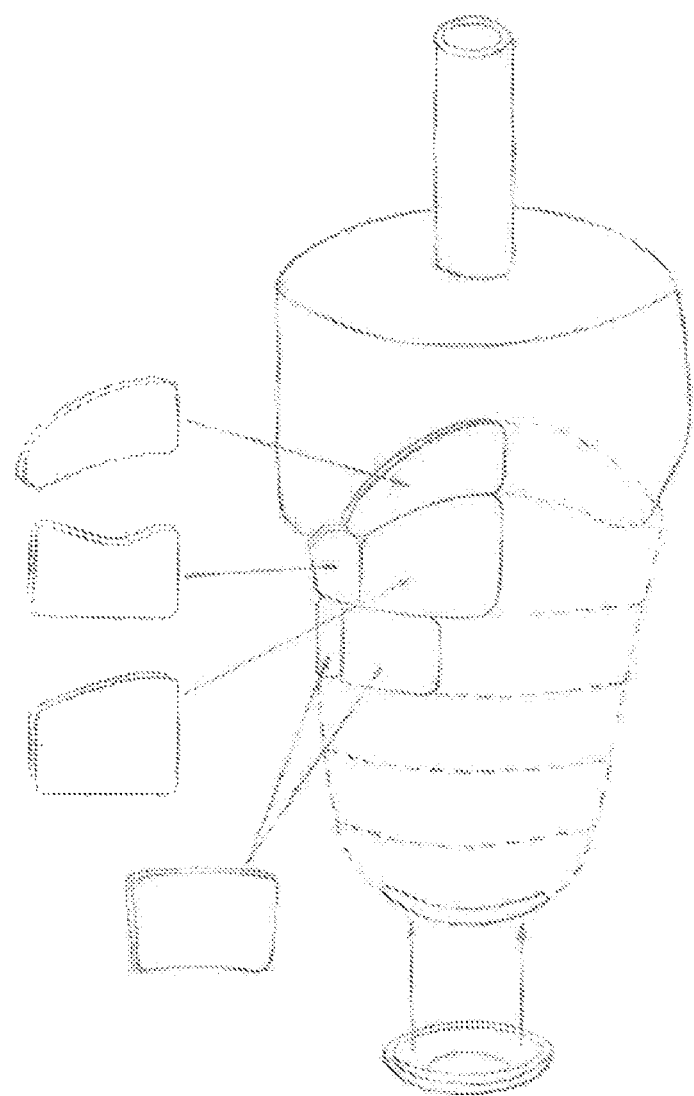
FIG. 6 is a drawing showing a method for assembling bladders in a desired configuration for use with the interface.
Figure 7:
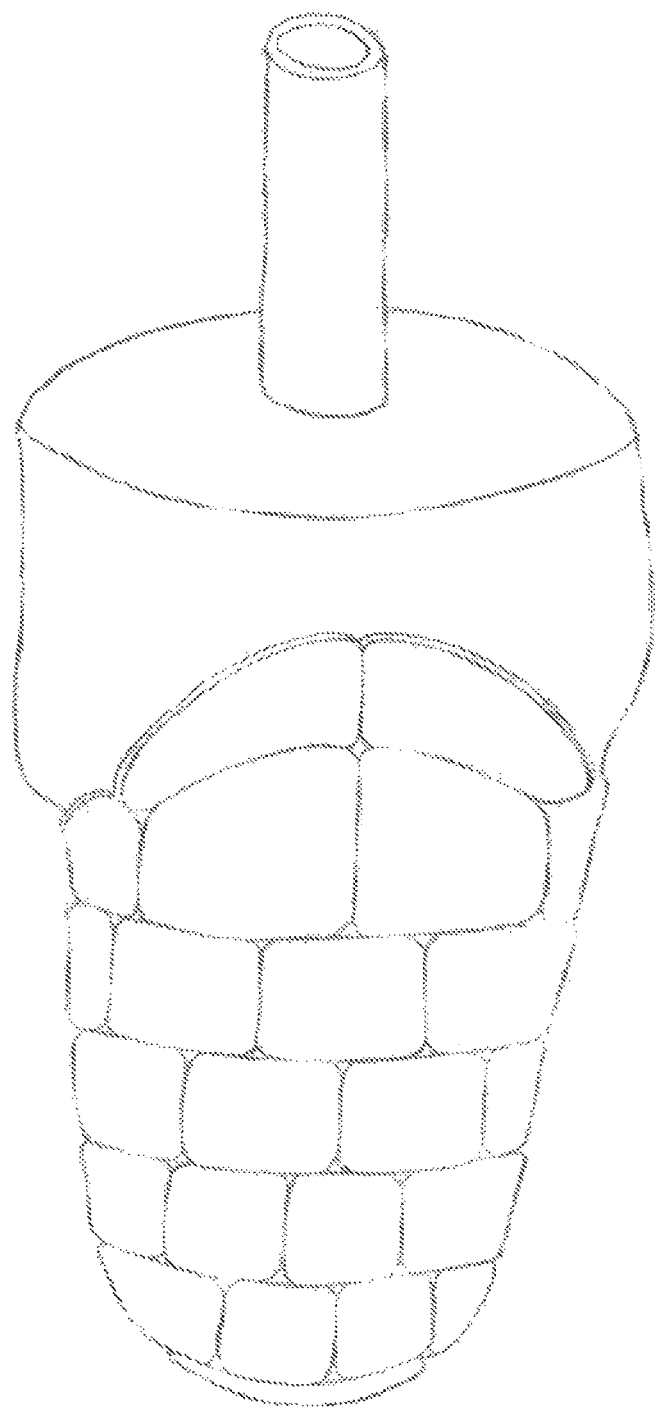
FIG. 7 is a drawing of a completed interface assembly.
Figure 8:
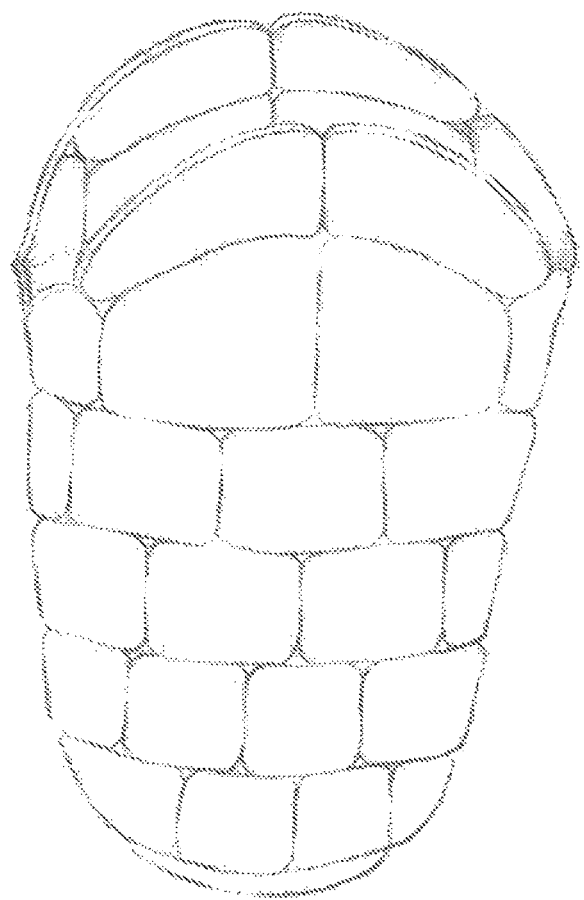
FIG. 8 is a drawing of the completed interface assembly removed from the model.

Although the packets preferably can even be assembled directly onto the patient's limb (which can be faster, involve less labor, and provide more certainty to get the correct fit), a plaster cast or other model of the limb can be made (see FIG. 5) and the packets assembled onto that model, or any other suitable fabrication method can be used. FIG. 6 illustrates one of the many methods that can be used to assemble the bladders into a desired configuration (using the cast/model of FIG. 5), FIG. 7 illustrates a completed assembly, and FIG. 8 illustrates that assembly removed from the model. Persons of ordinary skill in the art will understand that the assembly can be configured to cover the entire interface between the patient and the socket, just the posterior area of that interface, or whatever portion of the socket is desired and useful.

Some examples of the many ways the bladders can be assembled are gluing (or attaching/adhering/bonding/etc.) them together, first placing a thin layer of polyurethane or silicone on the mold (or the patient's limb) and then gluing/etc. the putty packets to that material, or gluing/etc. the bladders directly onto the interior of the socket. As indicated above, multiple layers can be fabricated and or intermixed, allowing even further customization.

For embodiments in which the bladders are assembled into a liner that is separable from the socket, it can be placed onto the patient's residual limb and then the patient can insert his/her residual limb (with the putty packet sleeve) into the socket (see FIG. 2). These or other methods can provide a packet assembly that is very smooth on the inside (the surface that contacts the patient's limb) and very hygienic.

For embodiments in which the bladders are formed into a curved assembly (such as a prosthetic socket liner), an "inside" surface of the packet (the one oriented toward the patient) can be made slightly smaller than the outside surface (the surface directed away from the patient, toward the socket's interior). By making this outer layer larger than the inner layer of the bladders, the risk of the bladder/packet wrinkling on the inside surface is reduced or eliminated.

Some of the many examples of the foregoing are illustrated in FIGS. 44-53, in which the bladder/putty packets preferably are shaped so that, when assembled within a prosthetic socket, they have little or no wrinkling, folds, or other deformations. In FIGS. 44-52, the upper portion of the Figure shows a top view of the element, and the lower portion shows an elevation view with preferred exemplary dimensions (among other things, these indicate some of the precise variation that can be achieved with various embodiments of the invention). FIG. 53 shows a perspective view of one such "custom-curved" packet. As indicated in those drawings, packet shapes can be customized for specific locations around the residual limb. Preferably, the "finished"

interior surface of the liner is as smooth as possible, to minimize the risk of causing irritation and/or discomfort to the amputee.

As indicated above, because embodiments such as just described can be so readily assembled into a relatively "custom" shape, amputees in any area of the world (including third world countries and/or war-ravaged areas) can benefit from the comfort and improved experience of having a custom-fitted liner for their prosthetic socket. To further facilitate such applications, and as indicated above, the bladders can be provided in a range of strategic sizes and shapes, including ones intended for placement on a "standard" portion of the limb. Such systems can require a minimum or reduced number of packets while still being sufficiently customizable for all or virtually all prospective patients. Although the bladders can be made in virtually any size, and although a larger number of relatively smaller packets would provide even more precise comfort and fit, at some point the design tradeoff becomes uneconomic or otherwise not helpful in certain situations. Among other things, too many bladders may reach a point that the system/device is too complicated and/or expensive to make/use/maintain/etc. Accordingly, preferably the sizes for certain applications are just sufficient to enable a desired range of liner assemblies with a desired degree of control/feel/function to the patient.

FIG. 9 illustrates an additional way in which the liner and system can be customized. An adjustable element such as an "oil dome" can be fabricated in any suitable manner, and then can be positioned between the socket interior and the patient and inflated/deflated to fine-tune the socket/liner fit on the limb. In FIG. 9, three components are shown in exploded view (see top part of FIG. 9), then assembled (see middle part) via heat sealing or other suitable means, and the affixed to a fluid source (see lower part). As indicated in that lower part of FIG. 9, oil or other suitable fluid preferably can be pumped into the adjustment element (and likewise preferably can be released or pumped out of the element) to vary the volume of the element. Persons of ordinary skill in the art will understand that, although the adjustment element is shown as an inflatable "dome," it can be provided in a wide range of shapes and configurations and still provide the utility described herein.

Figure 10:
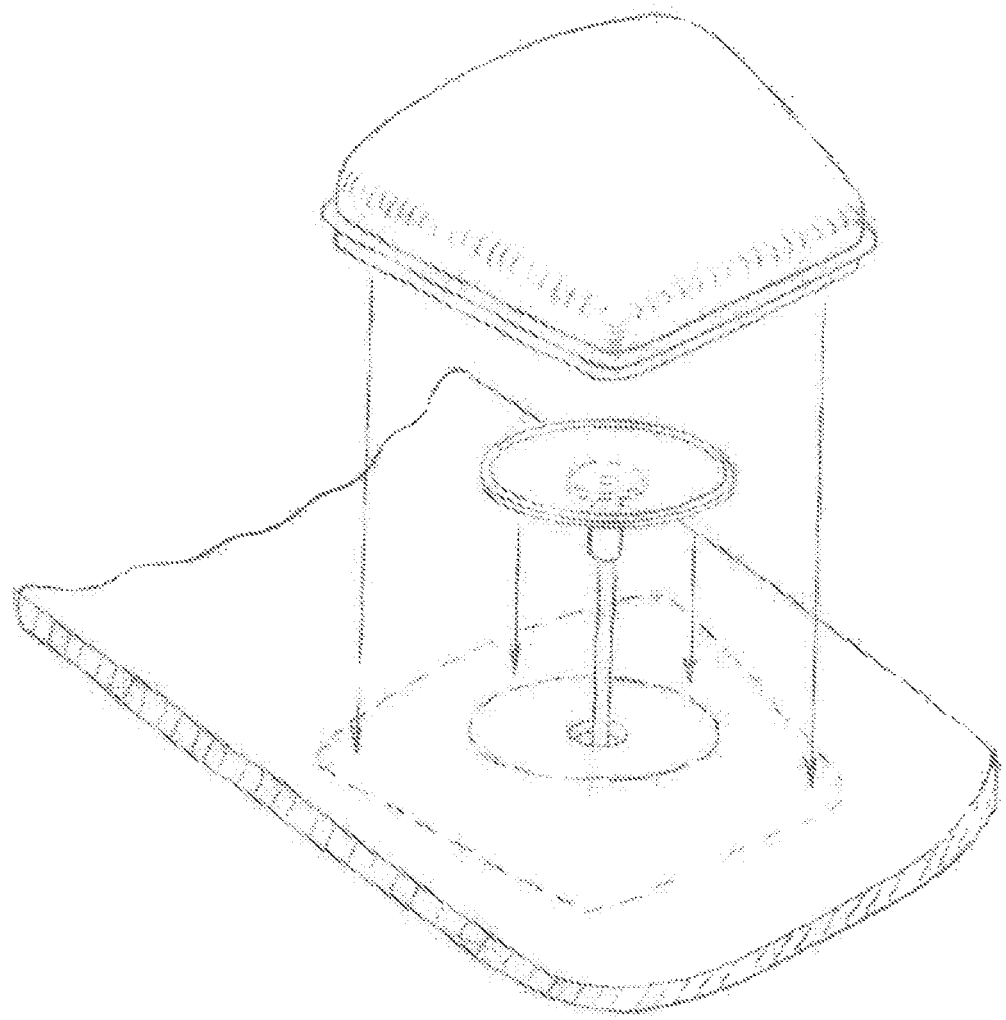
FIG. 10 is a drawing showing a perspective view of the inside of a part of a socket usable with the interface, showing assembly of an oil dome between the socket and an overlying bladder.
Figure 11:
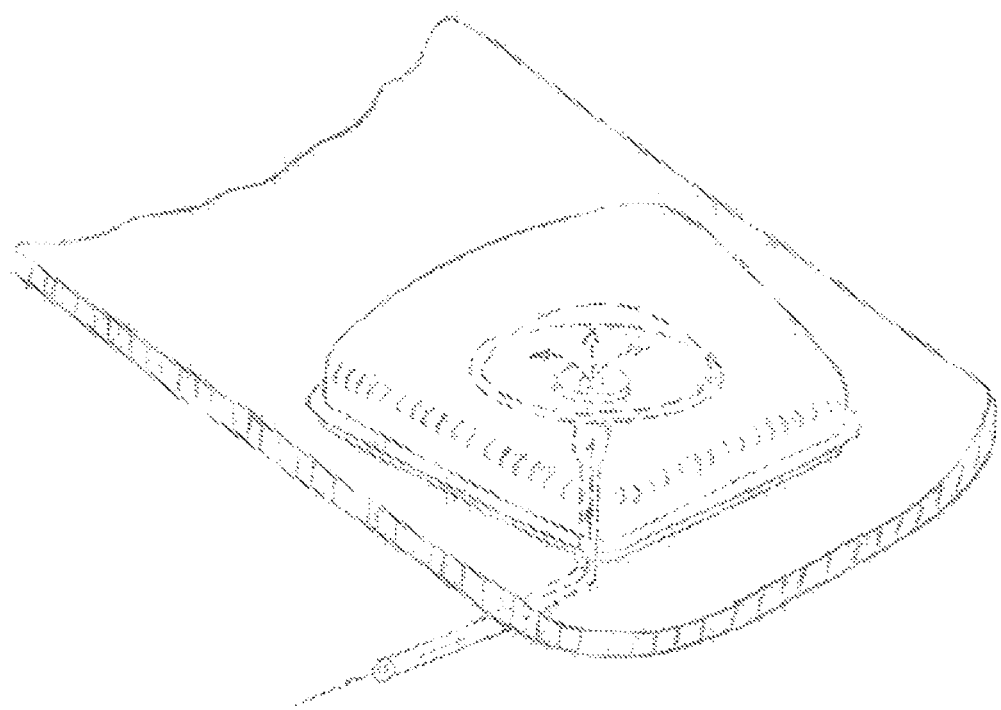
FIG. 11 is a drawing showing a perspective view of the inside of a part of a socket usable with the interface, showing assembly of an oil dome between the socket and an overlying bladder.

FIGS. 10 and 11 are perspective views of the inside of a part of a socket, illustrating how one of those oil domes can be assembled between the socket and an overlying bladder. In FIG. 10, the tubing for adjusting the volume of fluid in the dome is shown as passing through a hole in the wall of the socket, and FIG. 11 shows the completed assembly. Persons of ordinary skill in the art will understand that the adjustment of the dome's volume can be accomplished in a wide variety of ways (e.g., injection valves, syringes, etc.). Even for embodiments using tubing adjustment means (as shown in FIGS. 10 and 11), the socket can be formed with recessed paths on the interior surface to accommodate the tubing as it travels from the dome(s) to a fluid source/reservoir. Such embodiments would eliminate the need for holes through the socket. By locating the tubes in recesses in the socket wall, the tubes will not be pressed onto the wearer's residual limb. Further alternatively, some or all of the lines can be formed into the socket wall itself.

Figure 12:
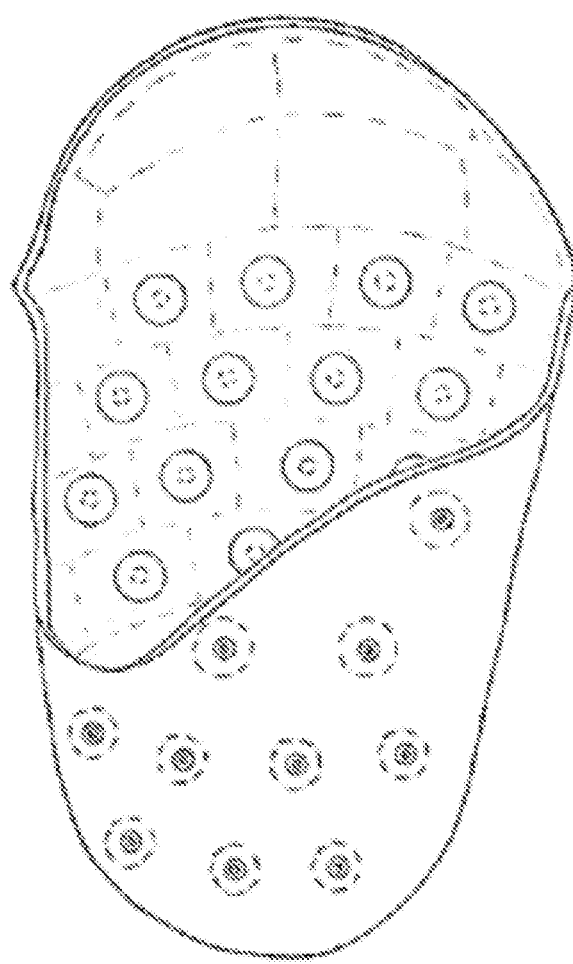
FIG. 12 is a drawing showing a partially cutaway perspective view of a plurality of adjustable domes bonded to the inside of a prosthetic socket and usable with the interface.
Figure 13:
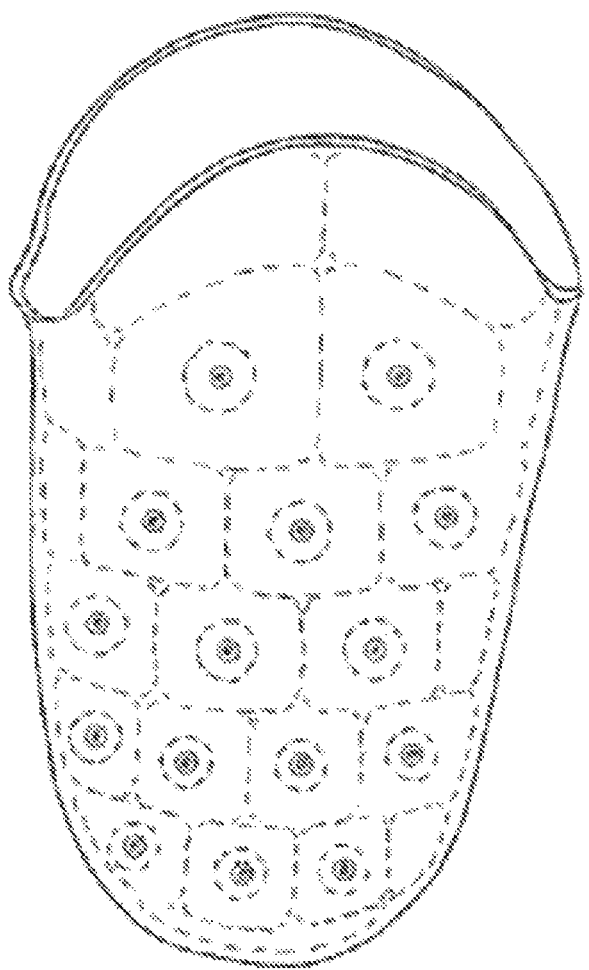
FIG. 13 is a drawing of the complete socket where a plurality of adjustable domes bonded to the inside of a prosthetic socket.
Figure 14:
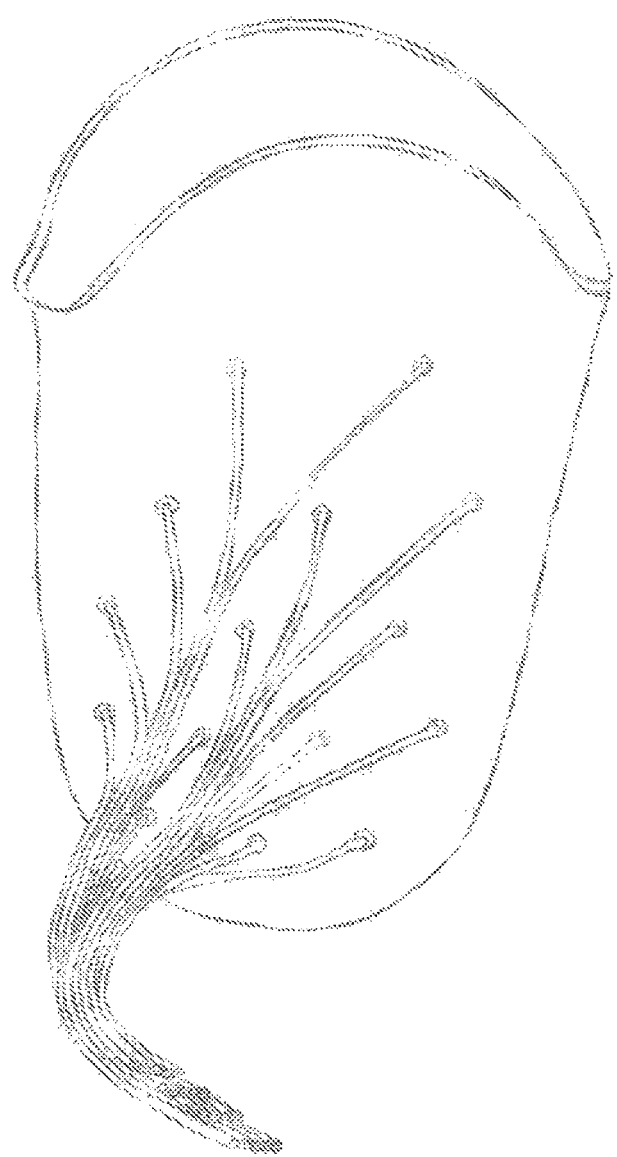
FIG. 14 is a drawing of the complete socket usable with the interface showing tubing connected to the various adjustable elements.
Figure 35:
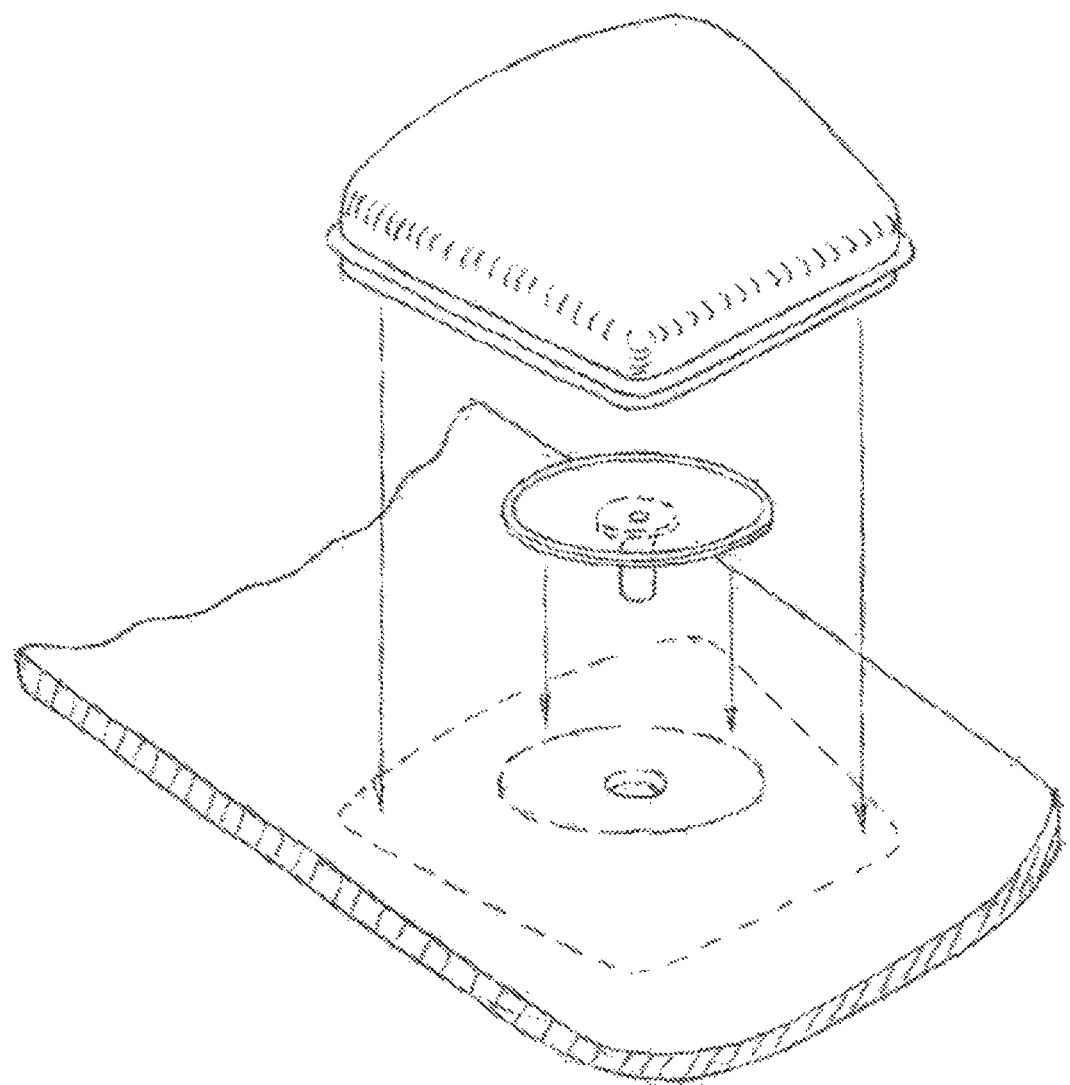
FIG. 35 is a drawing showing a self-sealing needle port usable with an interface to do one or more of fill and drain a fluid dome.
Figure 36:
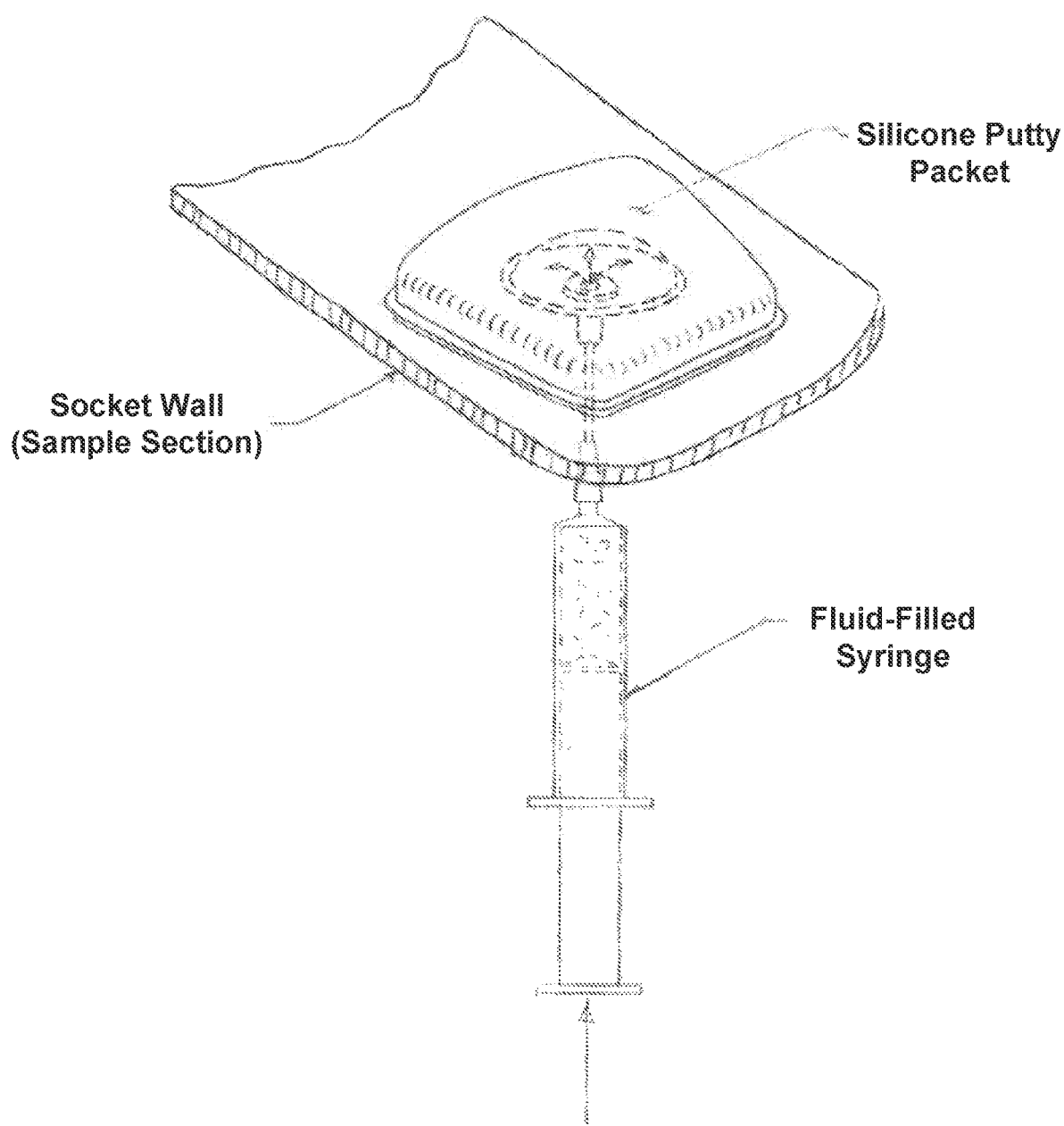
FIG. 36 is a drawing showing a self-sealing needle port usable with an interface to do one or more of fill and drain a fluid dome.
Figure 37:
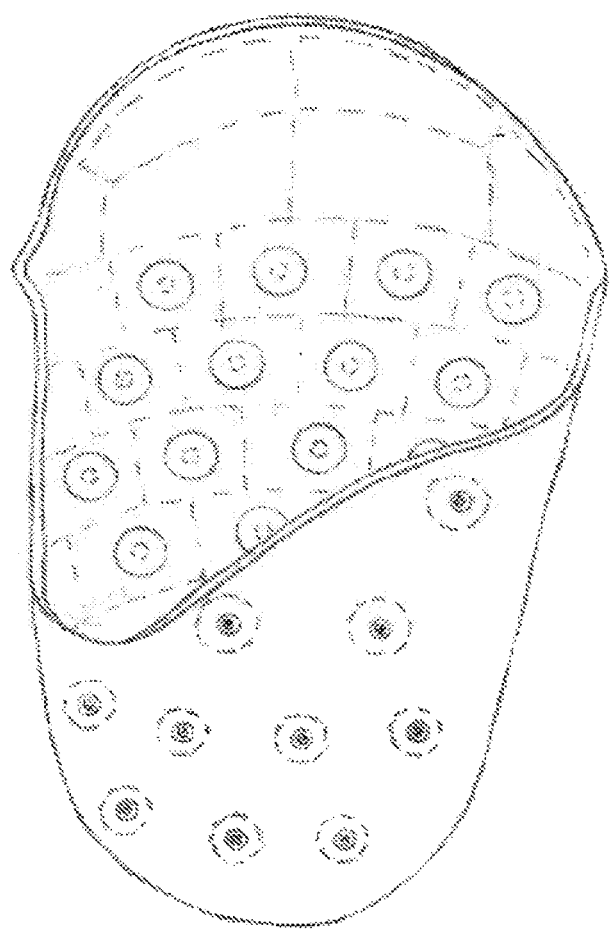
FIG. 37 is a drawing showing an interface assembled from multiple self-sealing needle ports.
Figure 38:
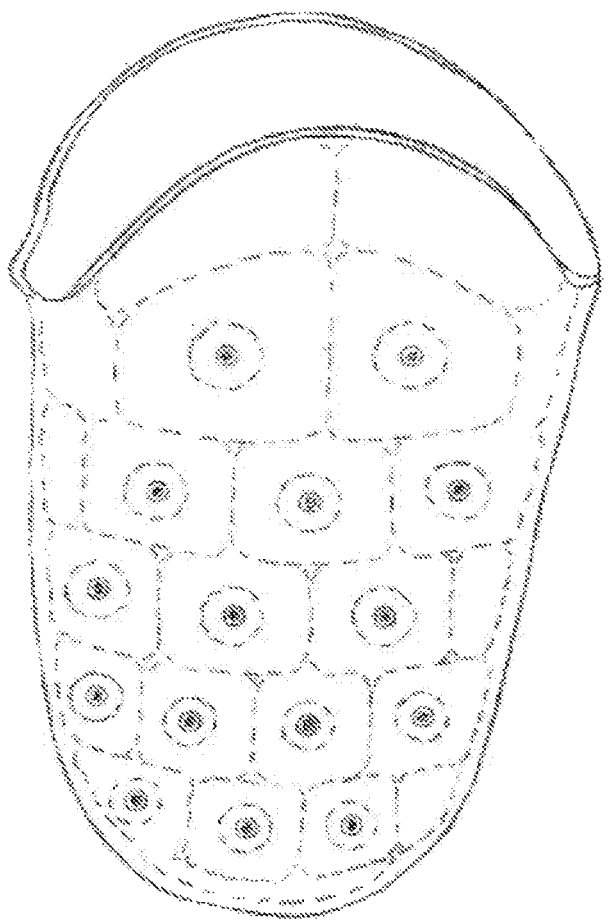
FIG. 38 is a drawing showing an interface assembled from multiple self-sealing needle ports.
Figure 47:
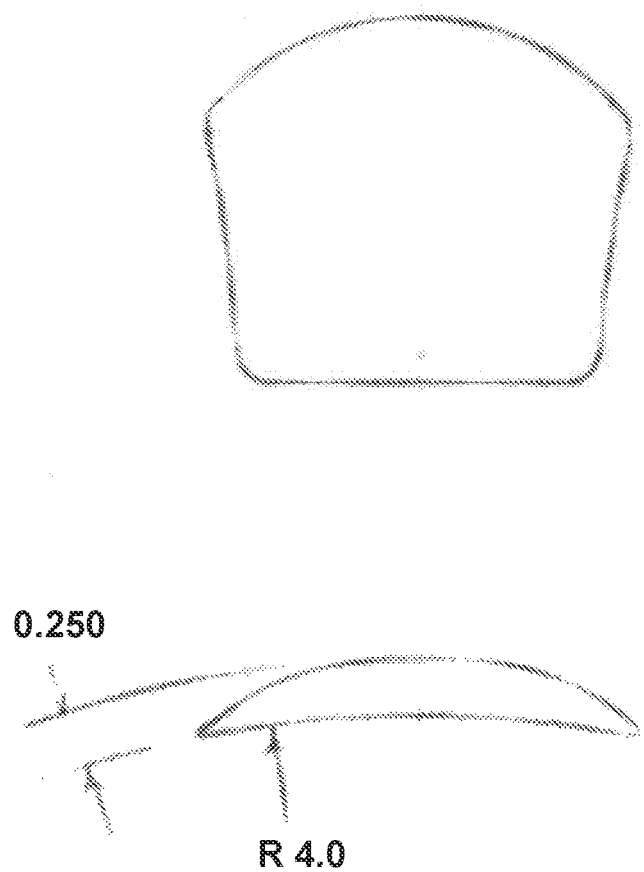
FIG. 47 is a drawing of an interface with bladder/putty packets that are shaped so that, when assembled within a prosthetic socket, wrinkling, folds, or other deformations are minimized.

FIG. 12 is a partially cutaway perspective view of a plurality of adjustable domes bonded onto the inside of a prosthetic socket. FIG. 13 illustrates the complete socket, and FIG. 14 shows how tubing may be connected to the various adjustable elements. Such tubes can penetrate the socket (as shown) or can be gathered and exit the socket through a hole in the bottom of the socket, or up and out the back/side of the socket. Among the many alternative embodiments of the invention, one or more (or all) of the tube or fluid lines may be routed from the bladders in a variety of ways (see examples illustrated in FIGS. 35-37). For embodiments in which the pump is external to the socket, the lines may be routed through a single hole 3602 the socket 3600 (near the bottom of the socket as mentioned above, or at some other convenient location). A single line 3504 can be used to fill/drain more than one dome/bladder 3502 (see again the examples of FIGS. 35-37). The tubes/lines may be assembled into one or more bundles 3506, a flat row of parallel lines 3702, or some other configuration, and draped up and over the back edge of the socket 3500. Still other examples include having one or more main lines 3604, 3704 from the pump reach the inside of the socket 3700 (through the socket wall, over it, or otherwise) and then having the one or more tube fill lines connected/manifolded to it at that "inner socket" location.

To facilitate ease of use, modularity, and other benefits, the various fluid and/or control components of the invention preferably include connectors that can readily and securely connect the various fluid lines and/or control wires. Among other things, this permits prosthetists, doctors, patients, and other persons to readily configure (and/or customize, modify, and/or repair) an overall prosthetic assembly. This can occur at virtually any time: the time of initial fitting; as the amputee is preparing to undertake a different physical activity; when different/newer components become available; etc. For economic, environmental, or other reasons, an amputee might even use some of the "connectable" components and not others (perhaps buying and using the socket with fluid line openings but waiting to buy an adjustable version of the insert, and in the meantime using a non-adjustable insert).

FIGS. 38 through 43 illustrate the use of self-sealing needle ports 3800, one of the many alternative ways to fill/drain 3902/3904 the pressure/volume modulating fluid domes 4102. FIGS. 38-41 show details similar to those discussed elsewhere herein, while FIGS. 42 and 43 show a liner assembled from multiple such packets/bladders. Persons of ordinary skill in the art will understand that the fluid in each bladder can be adjusted via use of a tool such as the hypodermic syringe 4106 shown in the drawings, or by any of a wide range of suitable alternatives. These self-sealing needle ports 3800 or the like can be used in lieu of a matrix of tubing, and/or in combination with sub-matrices of tubing and/or other approaches. In other words, certain bladders (adjacent to each other or not) and/or zones or areas of bladders can be provided with one method of adjustment (e.g., needle port(s) 3800 such as shown in FIGS. 38 through 43), while other bladders may have an on-board manually-adjusted tubing matrix, while still others may have computer-controlled adjustments, and yet others may be fixed and/or have yet another means of adjustment. Persons of ordinary skill in the art will understand that the invention can be configured into a wide variety of embodiments to accommodate a particular amputee and/or a particular activity, or both.

Certain embodiments and methods of the invention may include a tool or capability of measuring or monitoring the fluid pressure, as a supplement or at least partial replacement for feedback from the amputee regarding comfort. By adding a pressure gauge (for example, on the syringe and/or input lines), a prosthetist can at least approximate what is likely to be a comfortable pressure within a given bladder, at the time that the prosthetist is initially fitting the prosthesis or thereafter.

The location and number and size of the domes or other adjustment elements can be any of a wide range of suitable designs, and can be used to very precisely control and modify the fit and comfort of the socket on the patient. Persons of ordinary skill in the art will understand that the corresponding number and location of the fill line holes (if any) through the socket, and the number of fill lines through those holes (zero, some, or none of the holes may have lines placed through them), can be any of a wide range.

As indicated above, for embodiments in which the bladder assembly is separable from the socket (such as illustrated in FIG. 15), the patient can place his limb into the socket. In other of the many embodiments of the invention, bladders and/or adjustable elements are affixed to the socket's interior, and the patient inserts his/her limb into that assembled device. Preferably, when the adjustable domes are unfilled on the socket wall, they are very smooth and simply arranged.

Persons of ordinary skill in the art will understand that the invention can be practiced with adjustable elements and no bladders, with bladders and no adjustable elements, with some adjustable elements but some parts of the socket not adjustable or not even covered with a bladder, etc.

In use, the effective volume of liner "material" (and resulting pressure on the patient's limb) at any location around the socket can be precisely controlled by adjusting the fluid within one or more of the adjustable domes elements. Increasing the fluid in the dome results in an increase combined effective volume of the putty packet(s) overlying that dome. This increase volume results in a corresponding increase in pressure imposed on the patient's residual limb at that location. The invention thus allows the areas around the socket to be controlled independently and individually; and to be changed virtually at will.

Figure 16A:
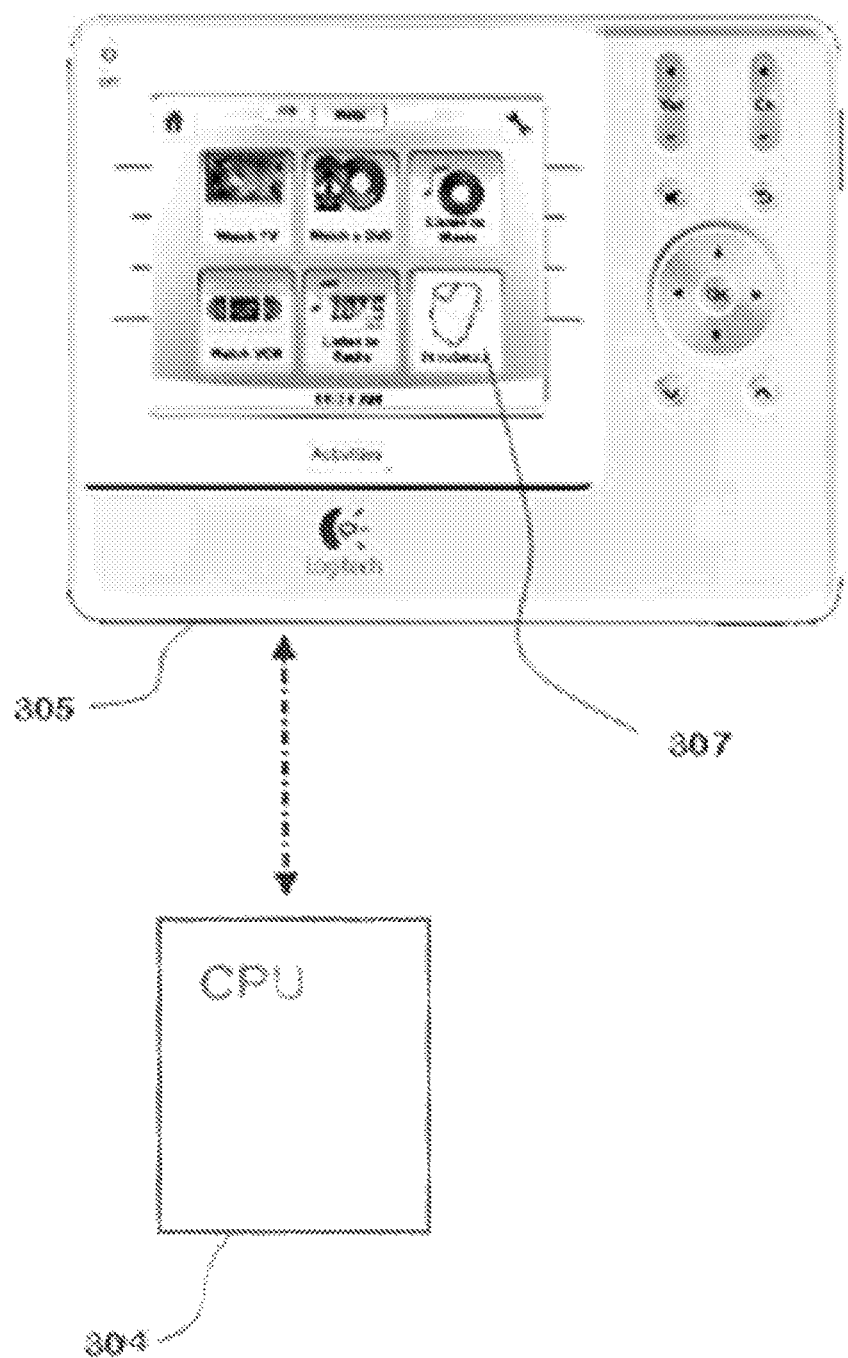
FIGS. 16A-16E is a set of five drawings illustrating examples of interfaces in which a microprocessor-controlled pump and valve system is mounted outside the socket.
Figure 16B:
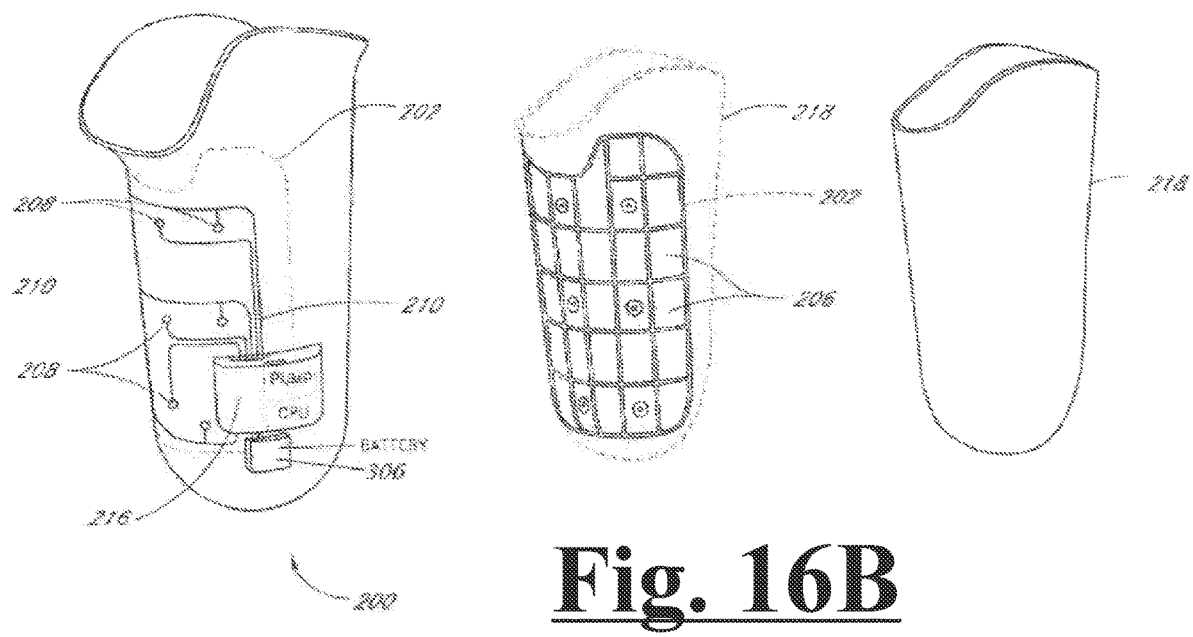
Figure 16C:
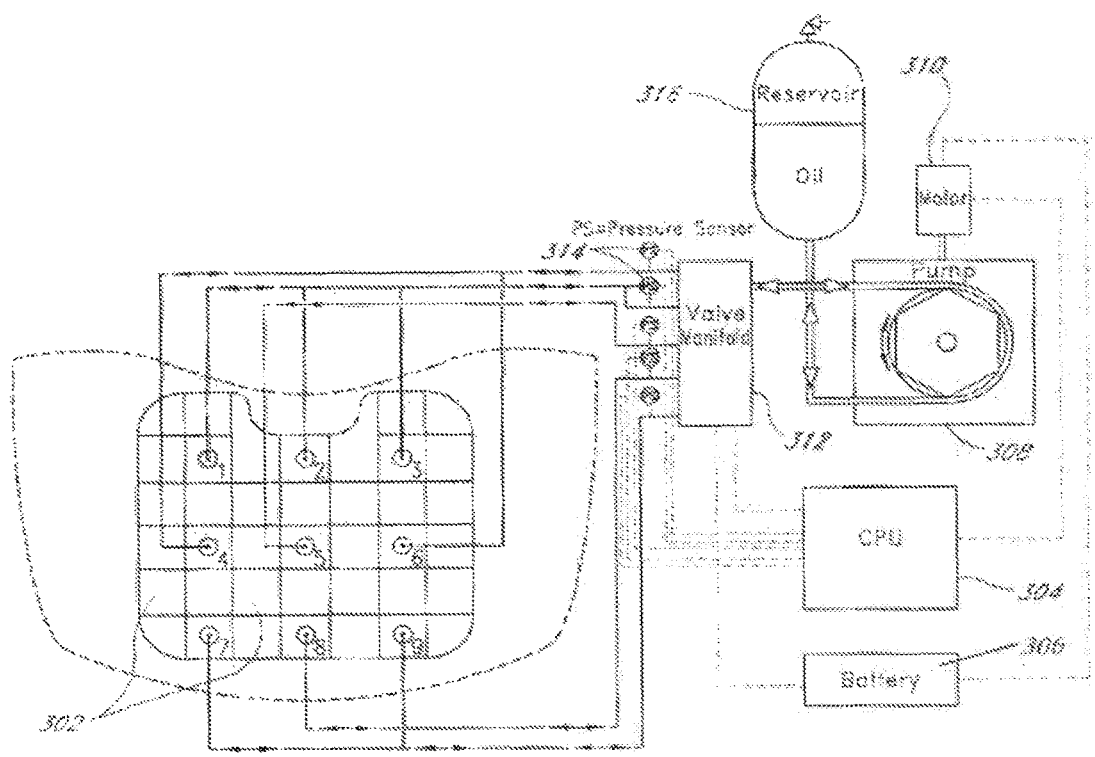
Figure 16D:
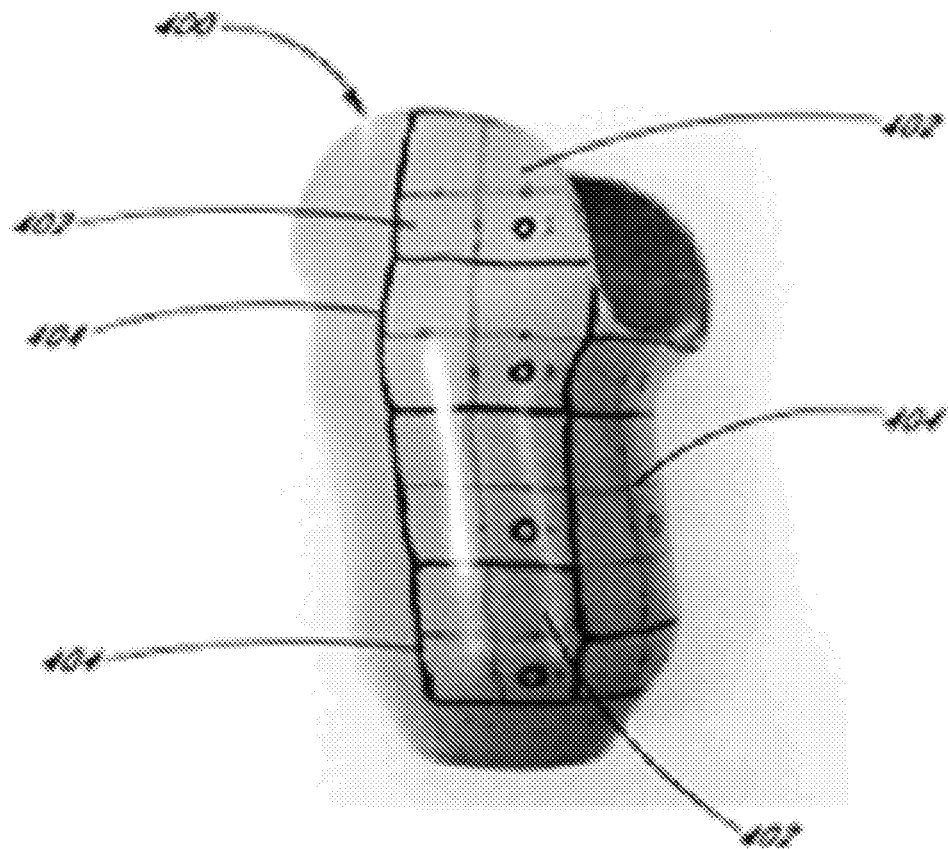
Figure 16E:
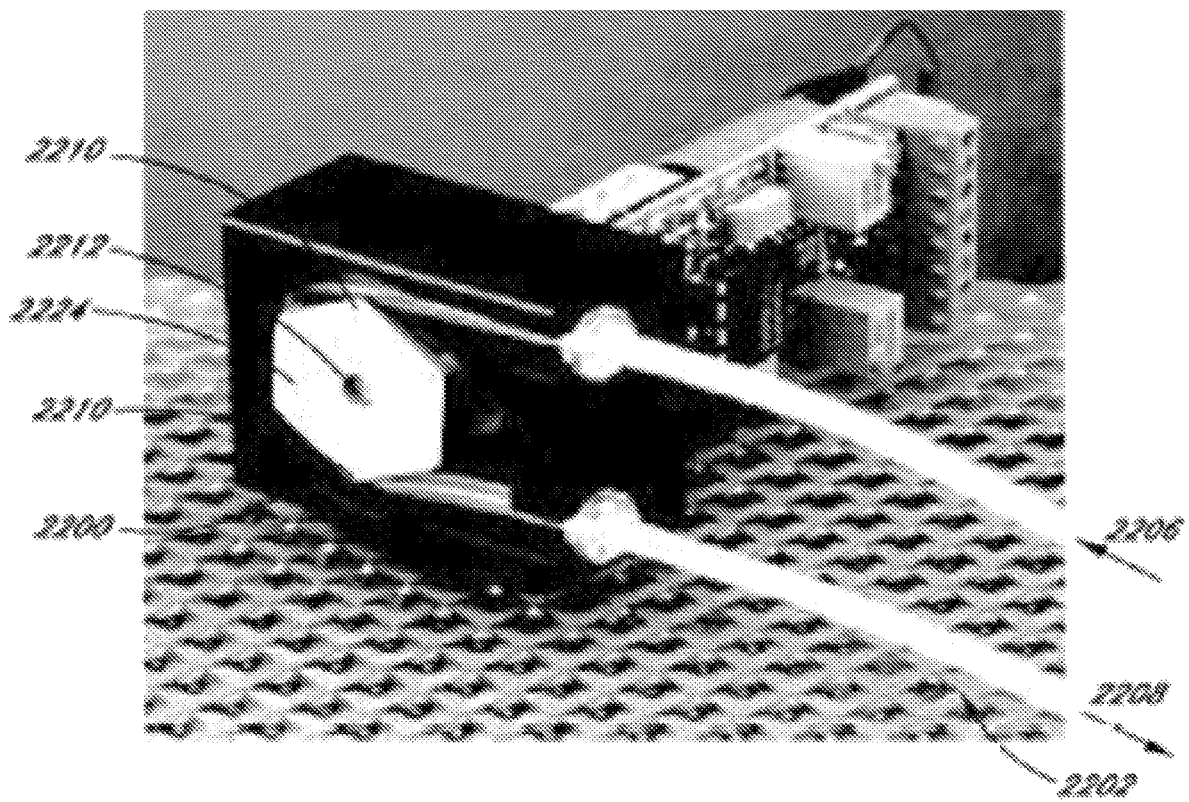
Figure 17:
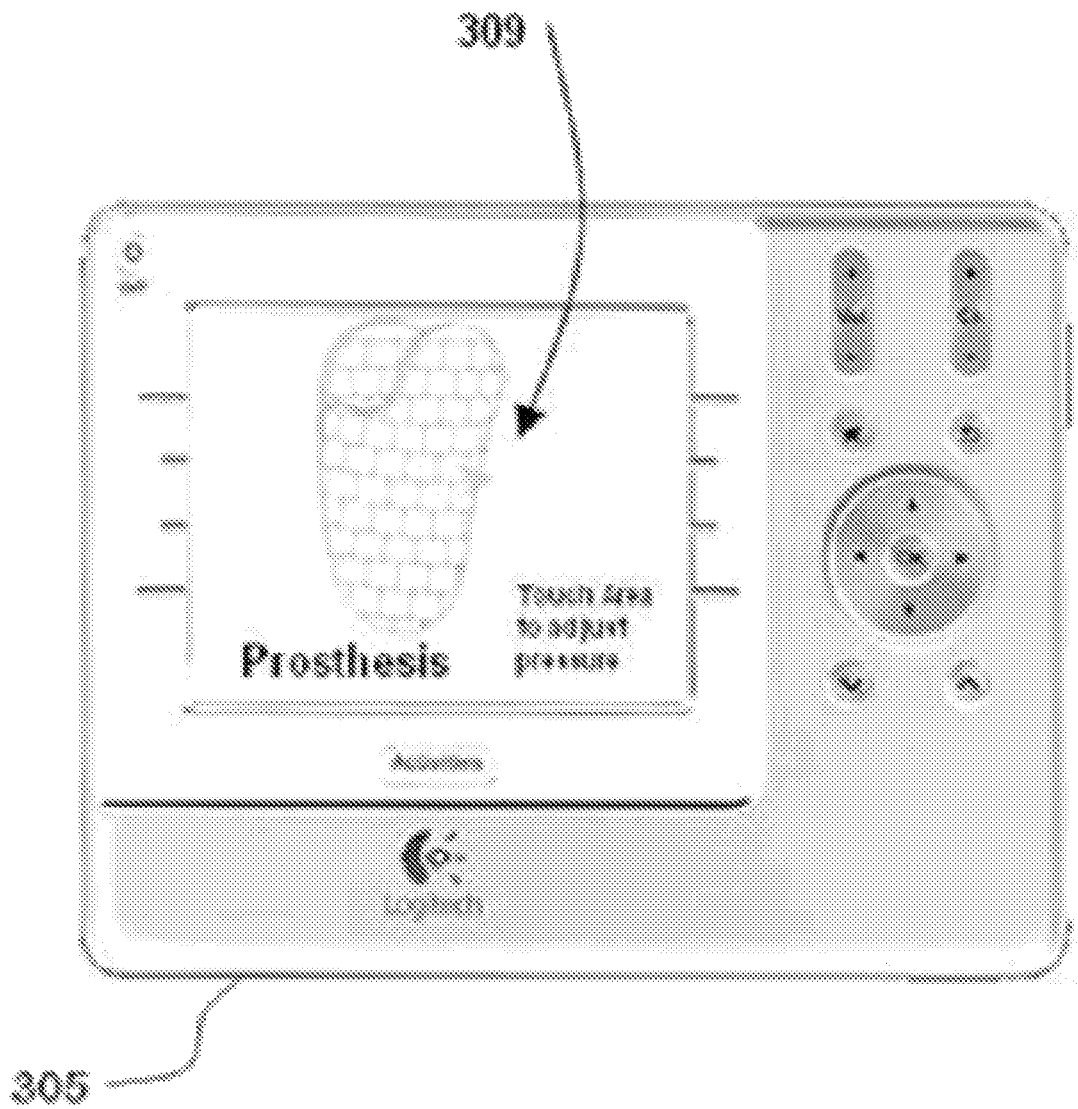
FIG. 17 is a drawing showing use of a remote control that is programmed to allow a patient using an interface to manually adjust pressure in a specific location.

In certain more sophisticated embodiments, a microprocessor-controlled pump and valve system 2200, 2202 can be mounted on the outside of the socket or otherwise, and pressure sensors 2210, 2212, 2224 can be positioned to sense various loading conditions within the sockets. Preferably, such systems can automatically manage and adjust the volume/pressure within each area of the socket by pumping fluid into and out of 2206, 2208 the adjustable bladder(s). FIGS. 16-16D illustrate examples of such elements and systems, and FIGS. 16 and 17 illustrate how a remote control (even a smart phone or IPHONE®/IPAD® 304) might be programmed to allow a patient to adjust the pressure in a specific location "manually," such as by touching the corresponding location 309 on a touch screen 305 controller 307.

In certain embodiments, the invention can adjust the volume/pressure in very small increments. The pressure in average fully loaded socket is in range of 4 to 8 psi; and the preferably the invention can make adjustments as small as ½ psi or less. Moreover, as indicated above, the inventions preferably can apply a target pressure value (such as may be prescribed by a physician); can reduce pressure on a targeted area or areas (tender areas, etc.), and otherwise provide a very high level of control over the fit and feel of the socket.

Persons of ordinary skill in the art will understand that the pumpable oil or other fluid preferably is manageable with pumps or similar devices, but by itself would tend to have very low viscosity (and therefore would tend to flow "away" from higher pressure areas, rather than supporting them. However, in certain embodiments of the invention such as those just described, the adjustment of the dome volume (with the low viscosity/pumpable oil or other fluid) "influences" the effective volume of the putty packet/bladder in that location, thereby influencing the pressure sensed by the patient at that location. Because the putty or other relatively high viscous material in the bladders does not tend to flow "away" easily, the relative position of the oil dome (empty, full or in between) preferably only effect the pressure felt by the patient. Otherwise, the patient preferably does not sense any change—the sensation on the patient's skin is the same whether there is some, none, or a lot of oil within the dome(s).

Preferably, the putty packets are small enough and thick enough to not "bottom out" when loaded. Persons of ordinary skill in the art will understand that this can be controlled and avoided by proper selection of the surface area and the thickness and other dimensions of the packets. As indicated above, other of the many embodiments of the invention can provide even further fine tuning, such as by using a layer of the putty packets by themselves (without any oil domes), using multiple such layers and/or intermixed and/or alternating layers of putty packets and oil domes, staggering/overlapping the putty packets, etc.

Alternative embodiments also include more complicated embodiments such as those illustrated in some of the other figures. As indicated above, for many applications, the simpler approach discussed above will be preferable. Other such more complex approaches are disclosed and discussed in my previous U.S. Pat. No. 7,655,049. Among other things, although such embodiments may provide certain benefits or be otherwise desirable in certain situations, such more complicated approaches are less amenable to use in third world situations, and perhaps less desirable for economical or other considerations. For example, if one of those more complicated bladders failed or was damaged, it likely would be relatively difficult to repair in a third world country. It also would be more difficult to keep clean in such environments.

Figure 18:
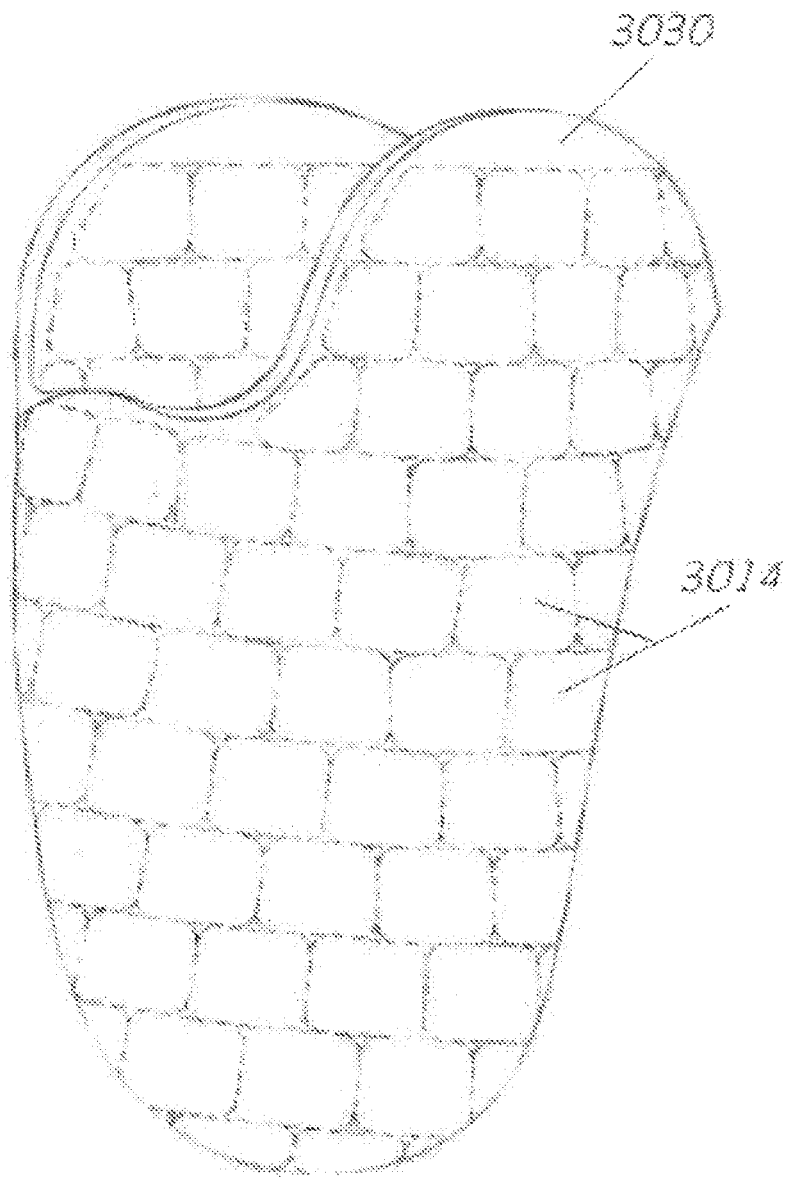
FIG. 18 is a drawing showing a generic size bladder usable with the interface.
Figure 19:
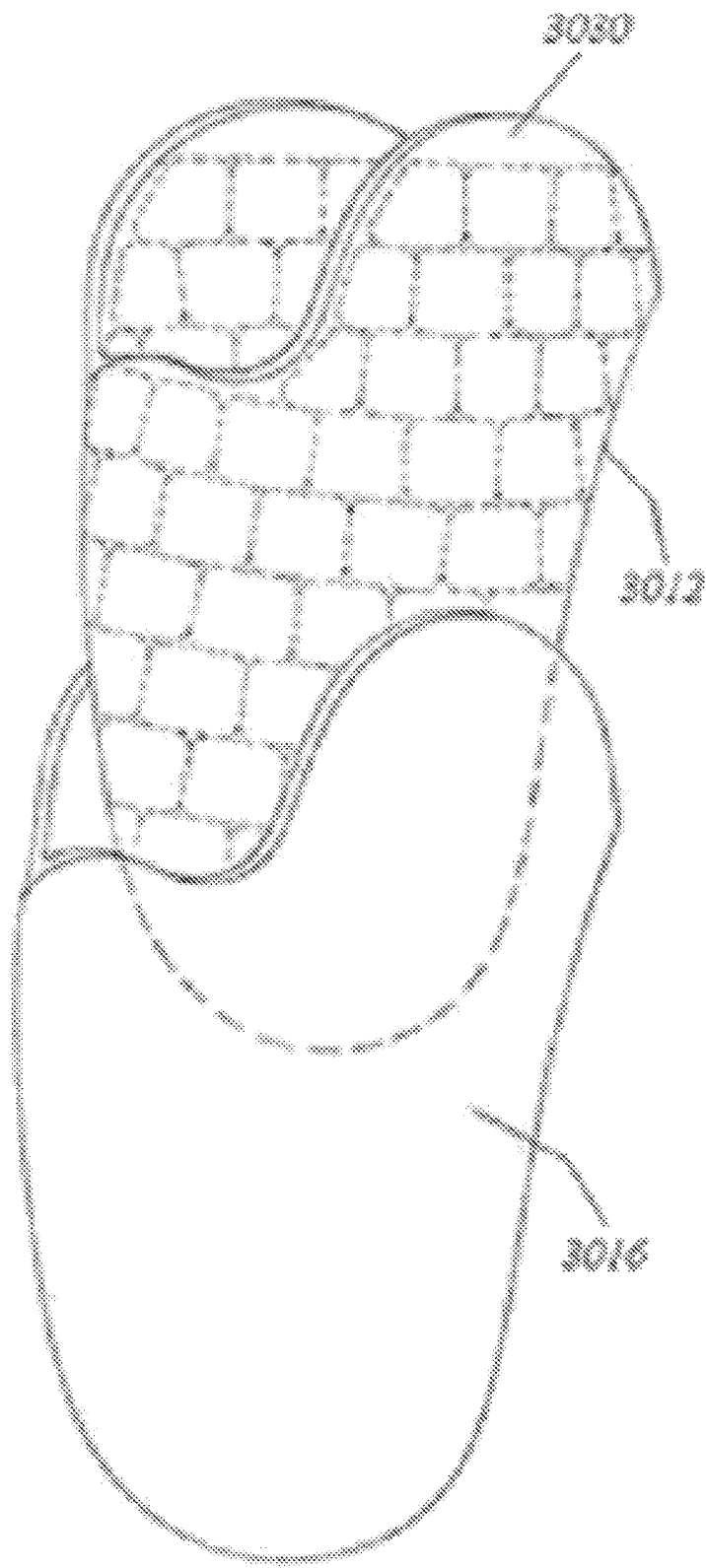
FIG. 19 is a drawing of a socket in an open area within the bladder, including a liner, both usable with an interface.
Figure 20:
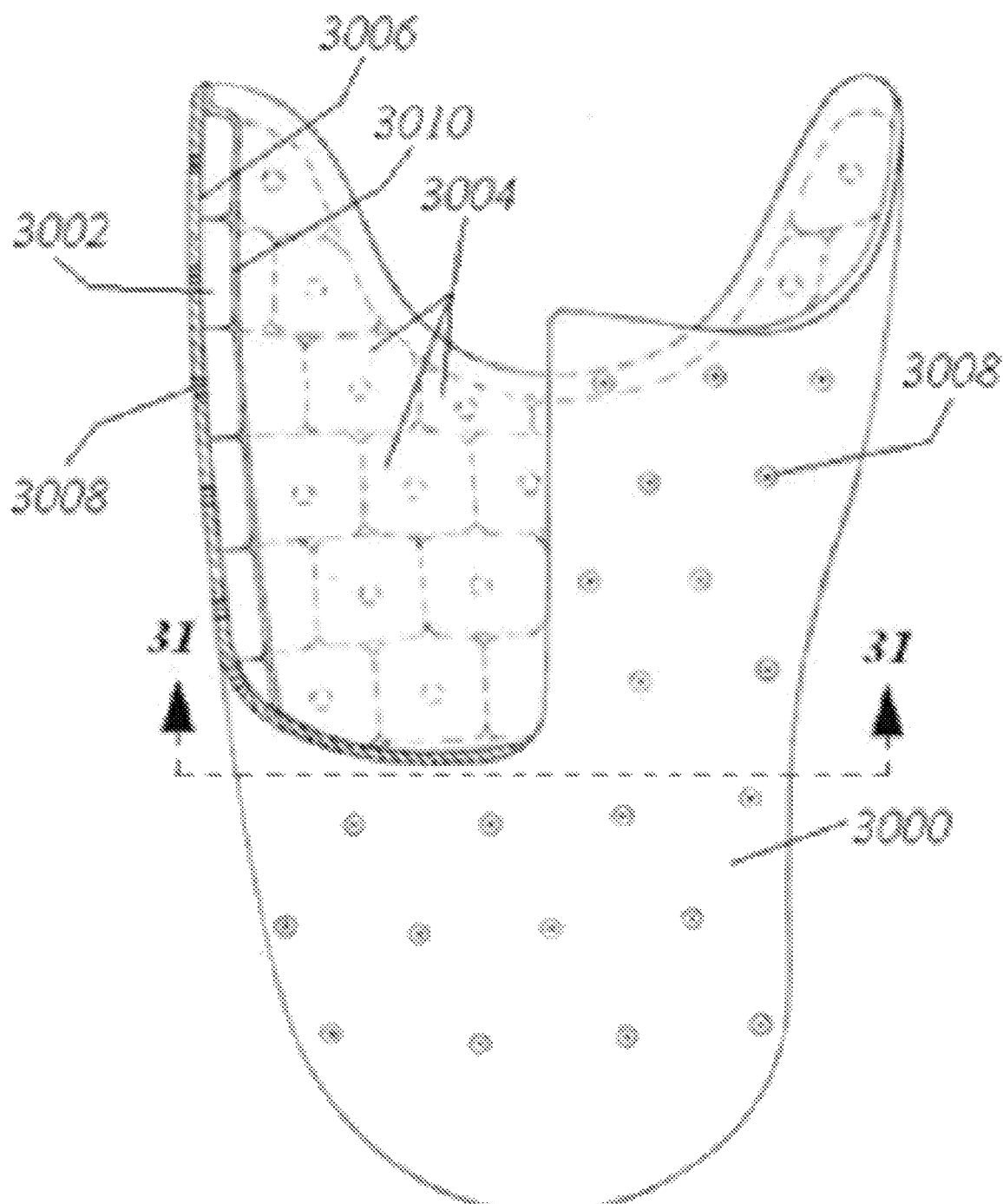
FIG. 20 is a drawing of a socket in an open area within the bladder, openings through the socket, and an internal barrier/sheath, all usable with an interface.
Figure 21A:
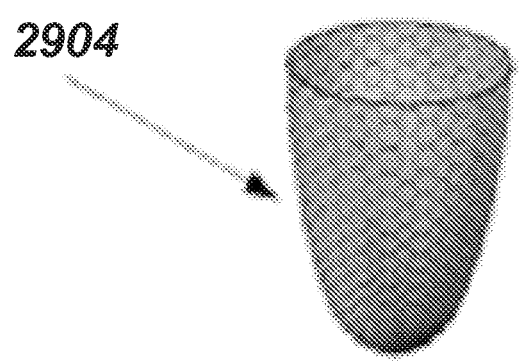
FIGS. 21A-21C are a set of three drawings of exemplary sockets usable with an interface.
Figure 21B:
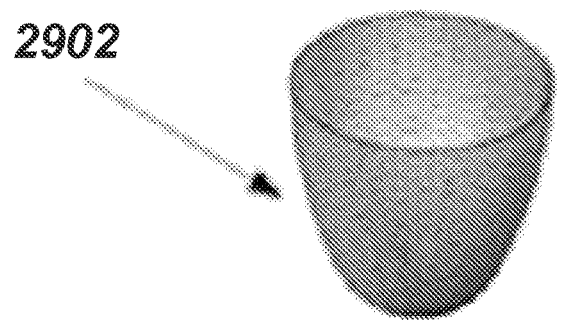
Figure 21C:
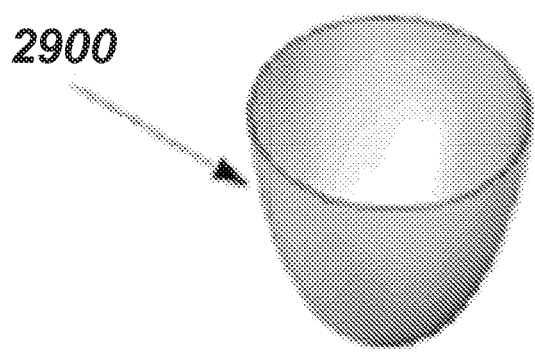
Figure 22:
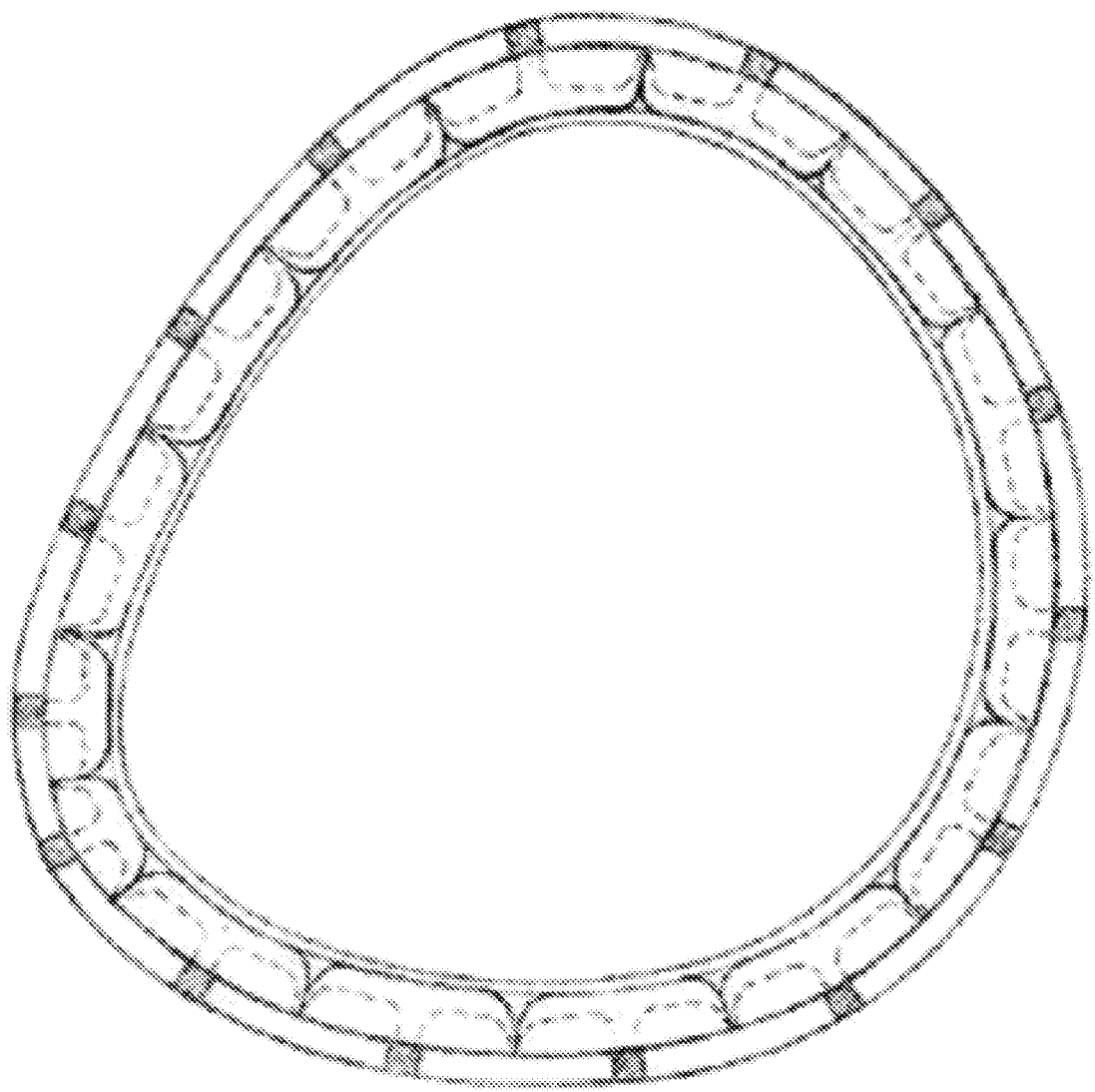
FIG. 22 is a sectioned view of a socket and liner assembly usable with the interface.
Figure 23:
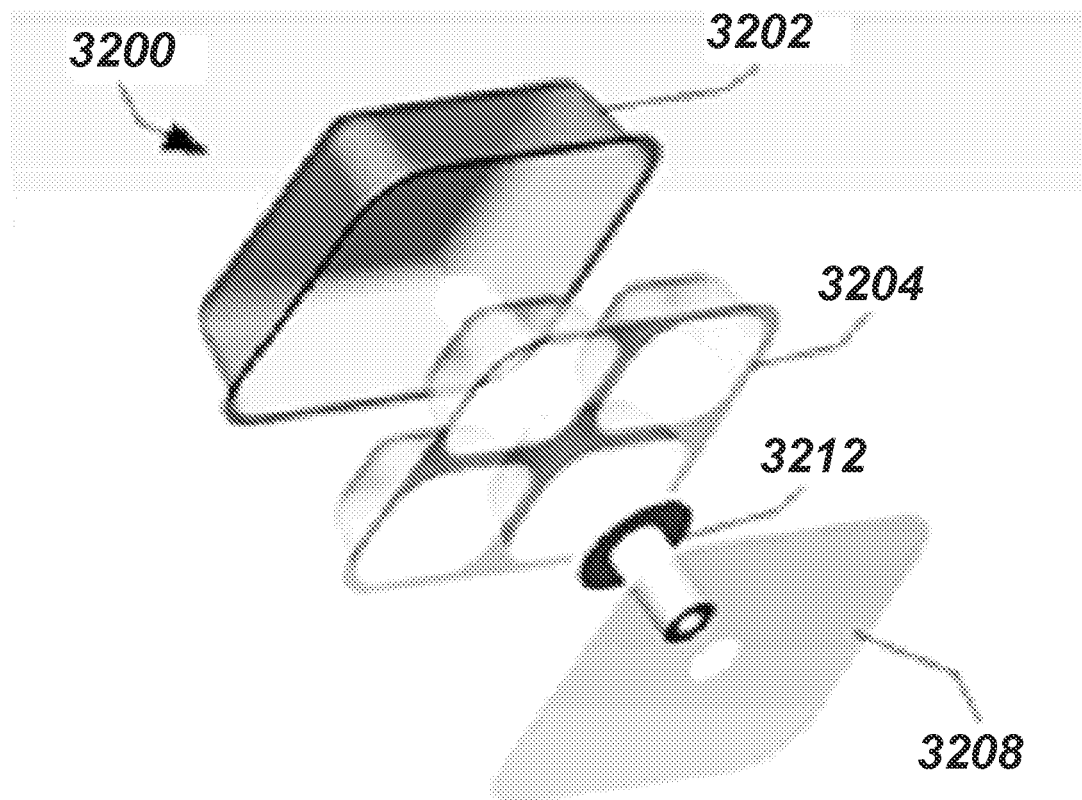
FIG. 23 is a drawing of an interface comprising both a larger bladder and smaller bladders.
Figure 24:
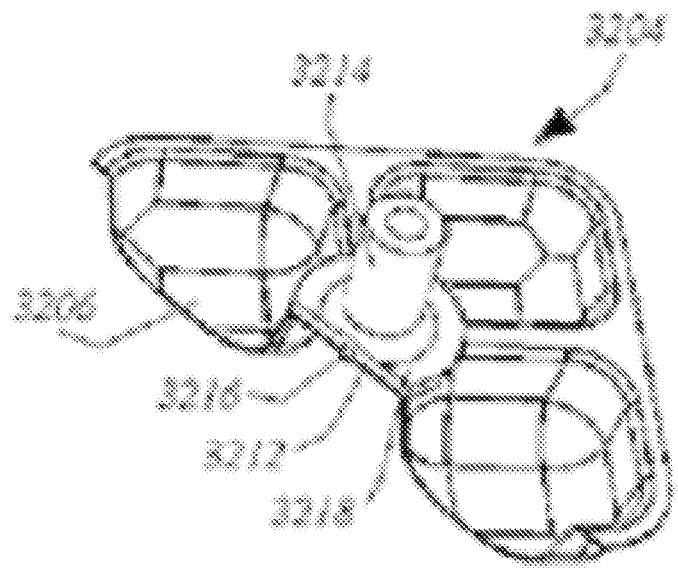
FIG. 24 is a drawing of a small bladder usable with the interface, including tubing connectors and a flange operably connected to the bladder.
Figure 25A:
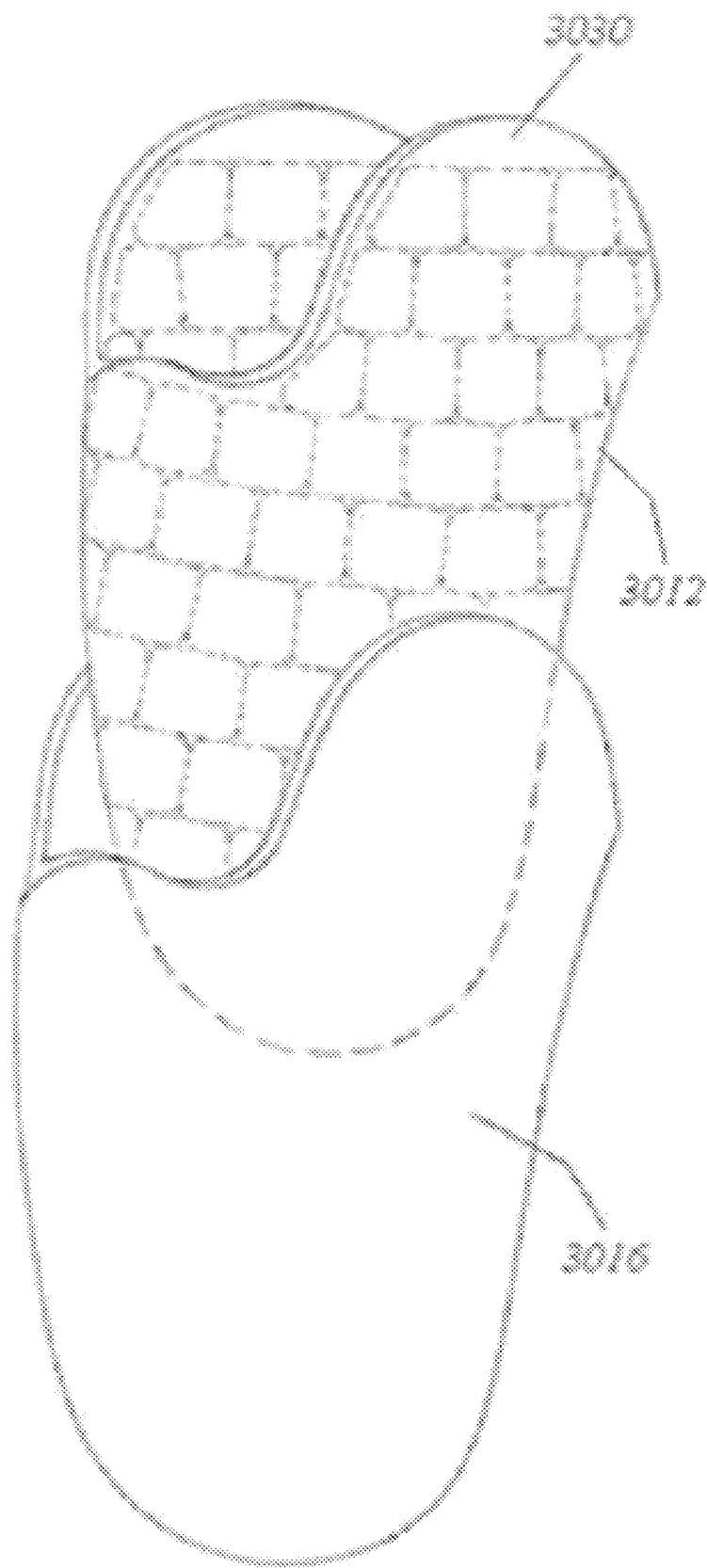
FIG. 25A is a drawing showing a generic size bladder usable with the interface.
Figure 25B:
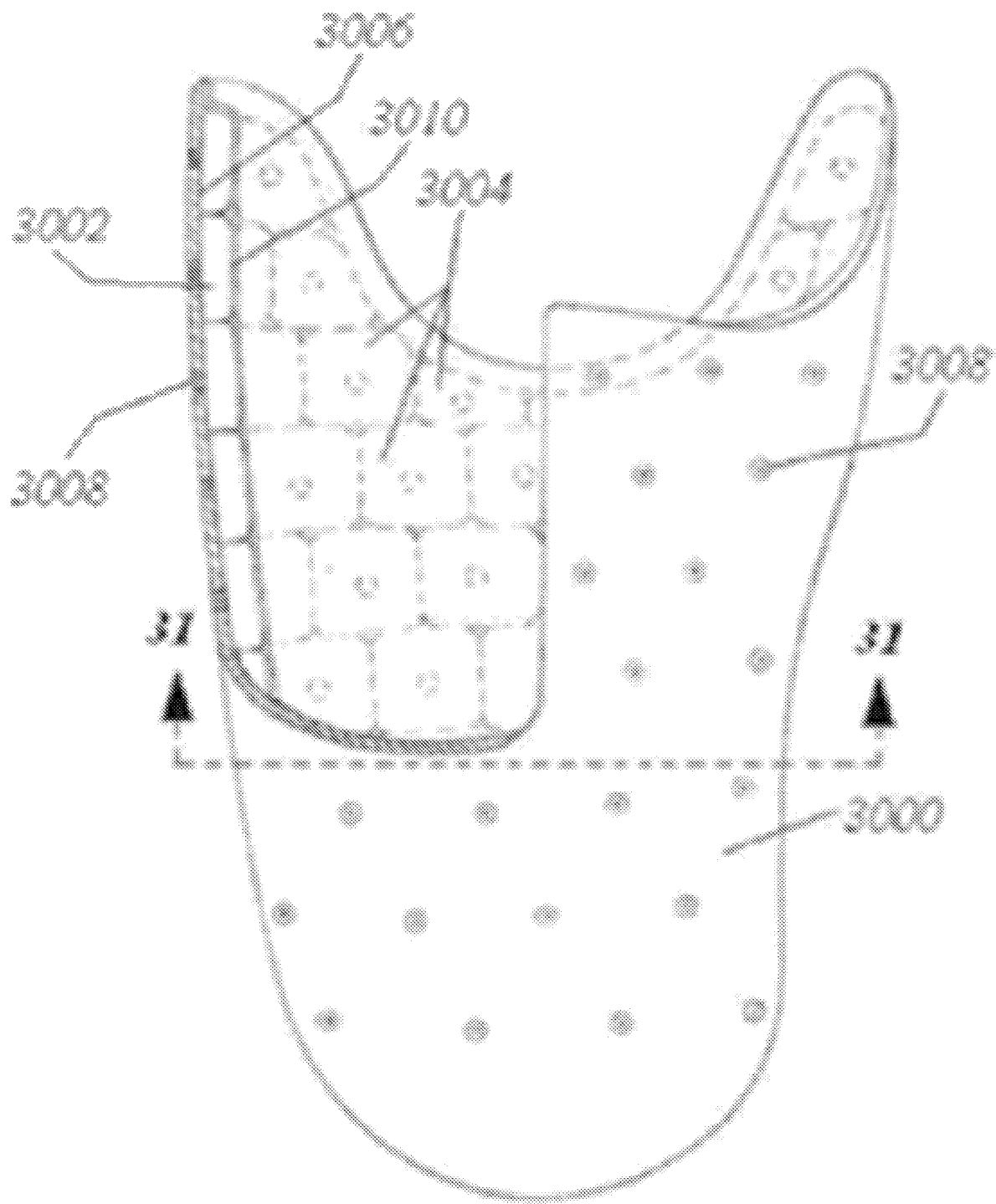
FIG. 25B is a drawing showing an interface using a generic size bladder.
Figure 26A:
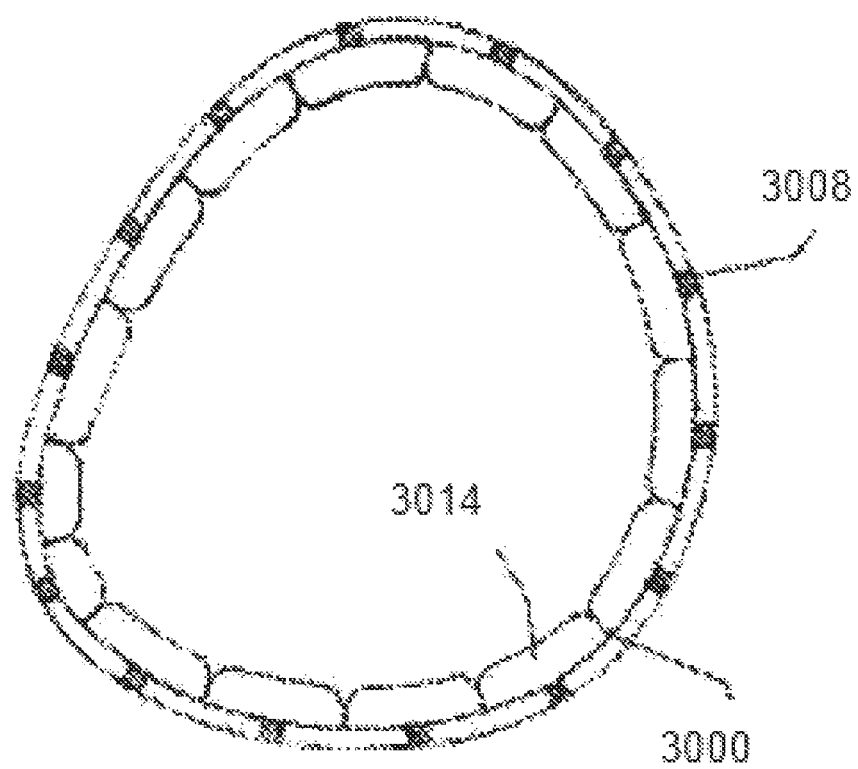
FIG. 26A is a drawing providing a sectioned view of a socket and liner assembly usable with the interface.
Figure 26B:
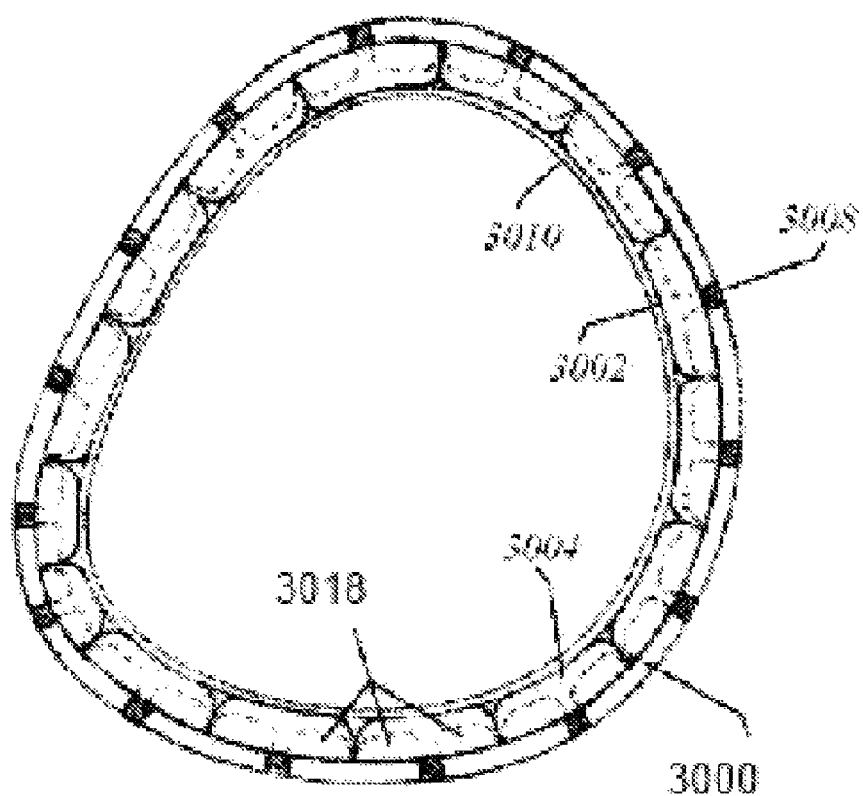
FIG. 26B is a drawing providing a sectioned view of a socket and liner assembly of an interface in which valves fill the holes and allow adjustment of the bladders.
Figure 26C:
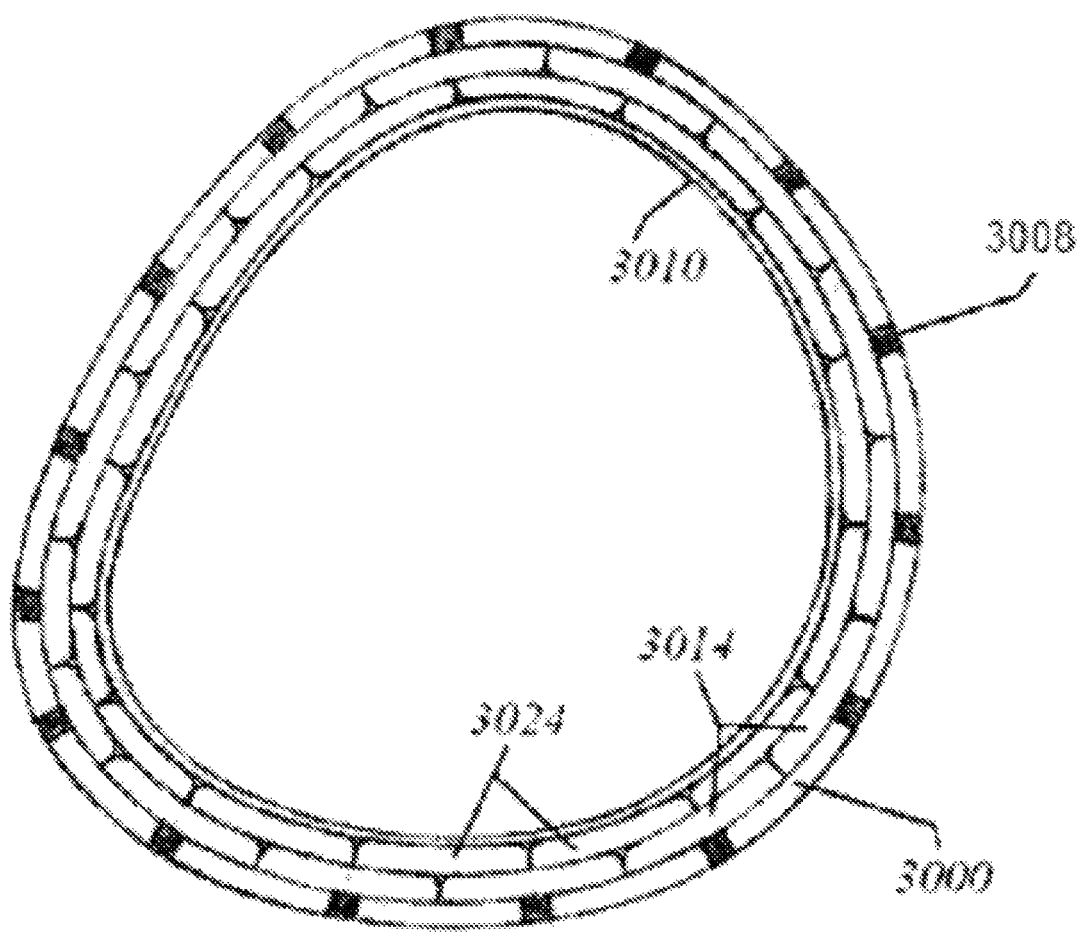
FIG. 26C is a drawing providing a sectioned view of a socket and liner assembly of an interface in which valves fill the holes and allow adjustment of the bladders.
Figure 27A:
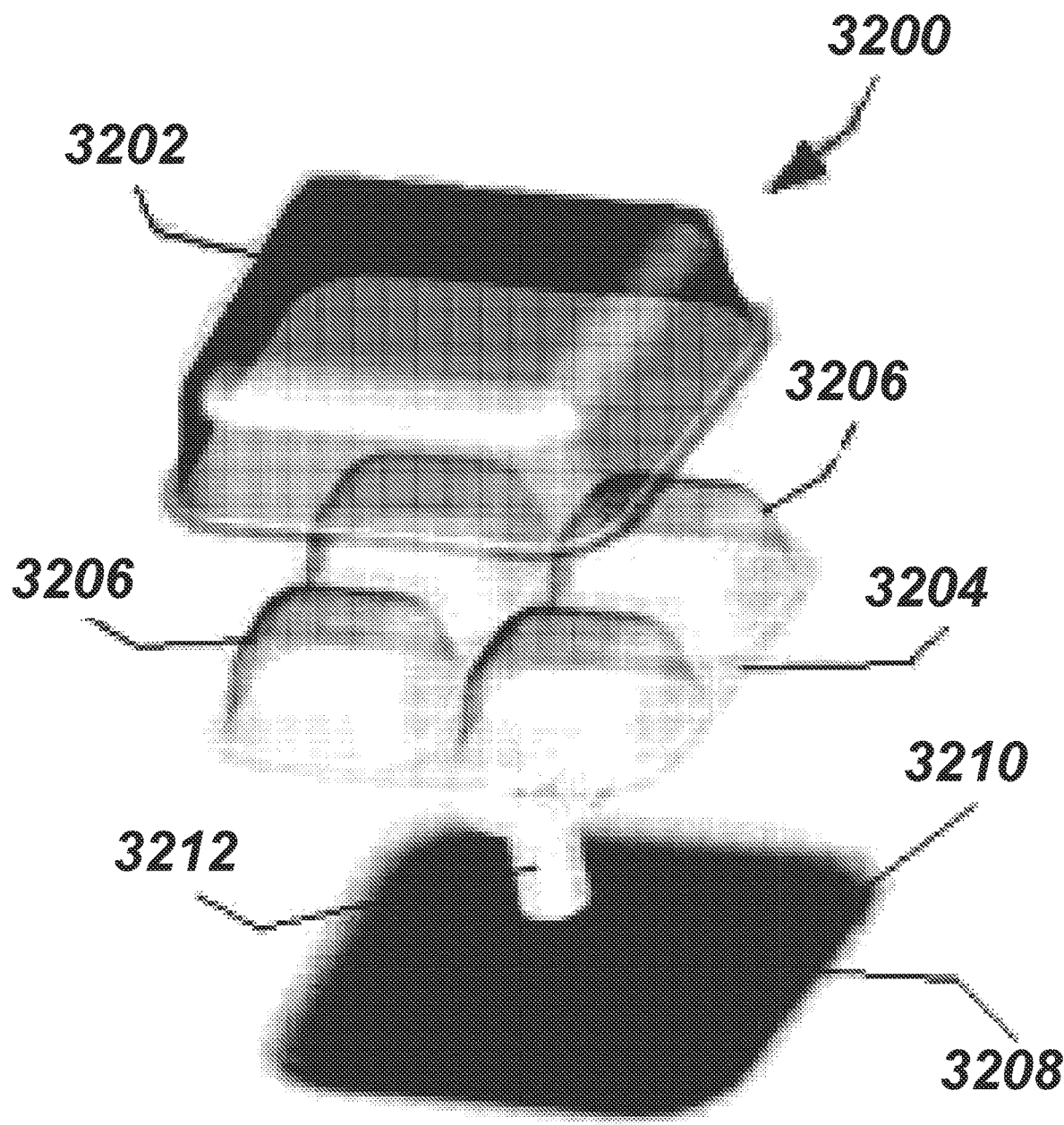
FIG. 27A is a drawing depicting an interface using an integrally formed bladder assembly.
Figure 27B:
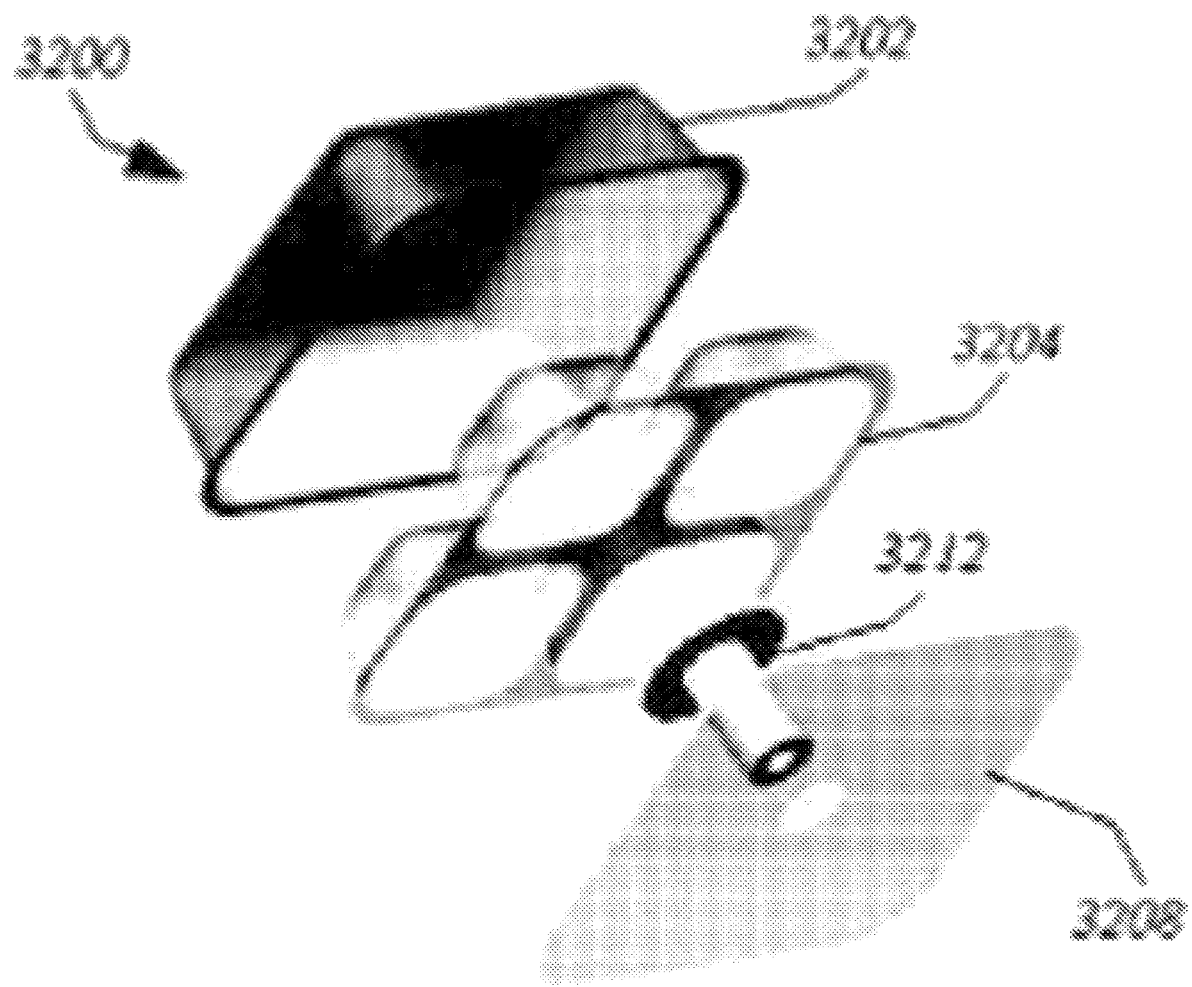
FIG. 27B is a drawing depicting an interface using an integrally formed bladder assembly.
Figure 27C:
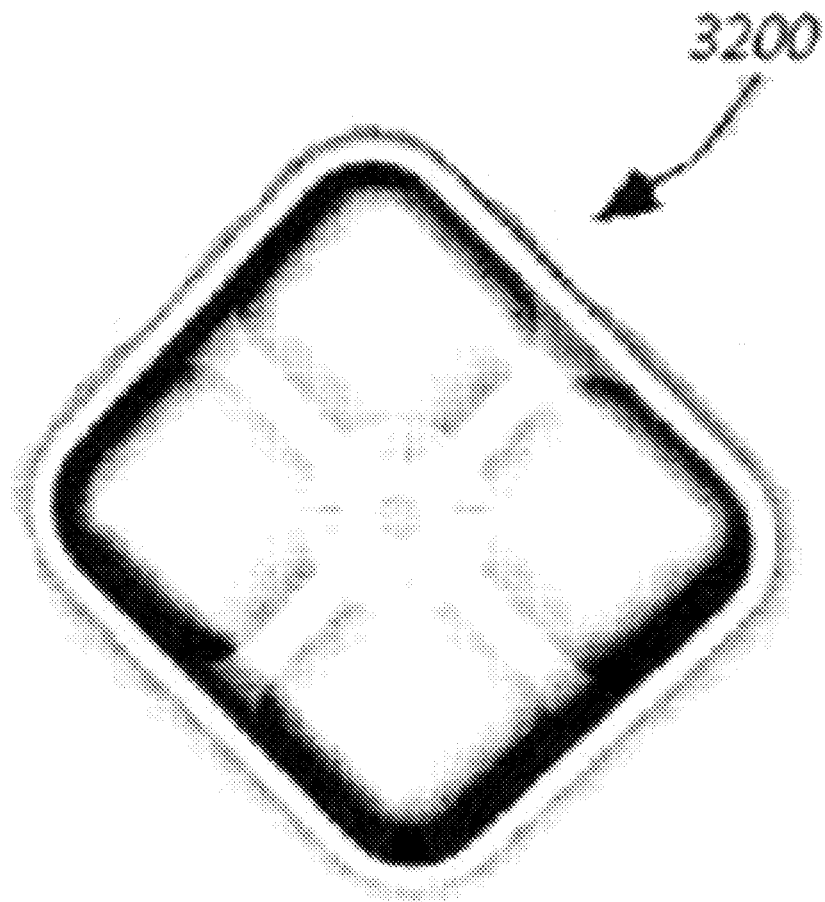
FIG. 27C is a drawing depicting an interface using an integrally formed bladder assembly.
Figure 28A:
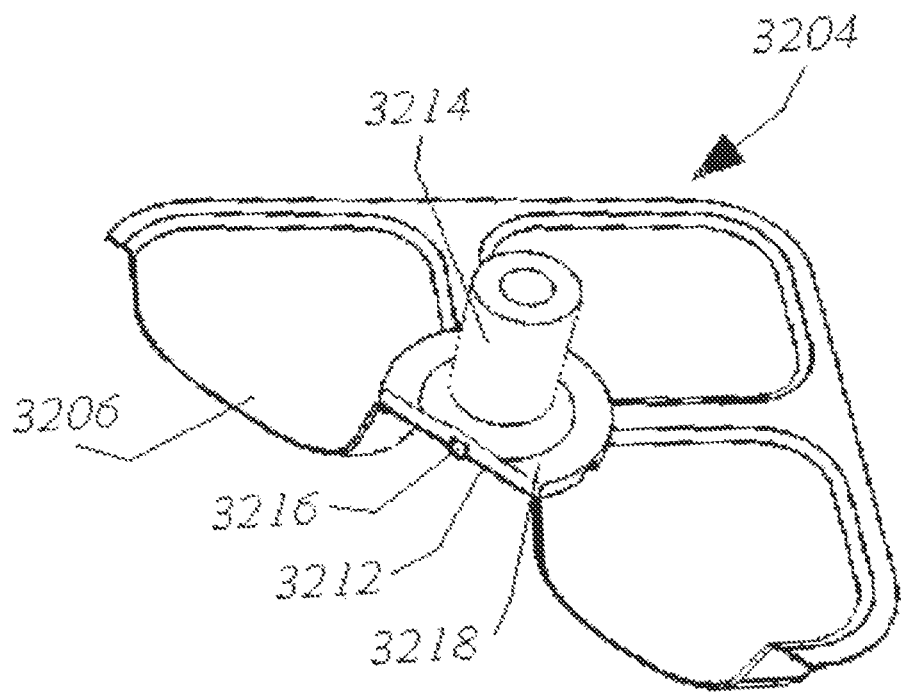
FIG. 28A is a drawing of a small bladder usable with the interface, including tubing connectors and a flange operably connected to the bladder.
Figure 28B:
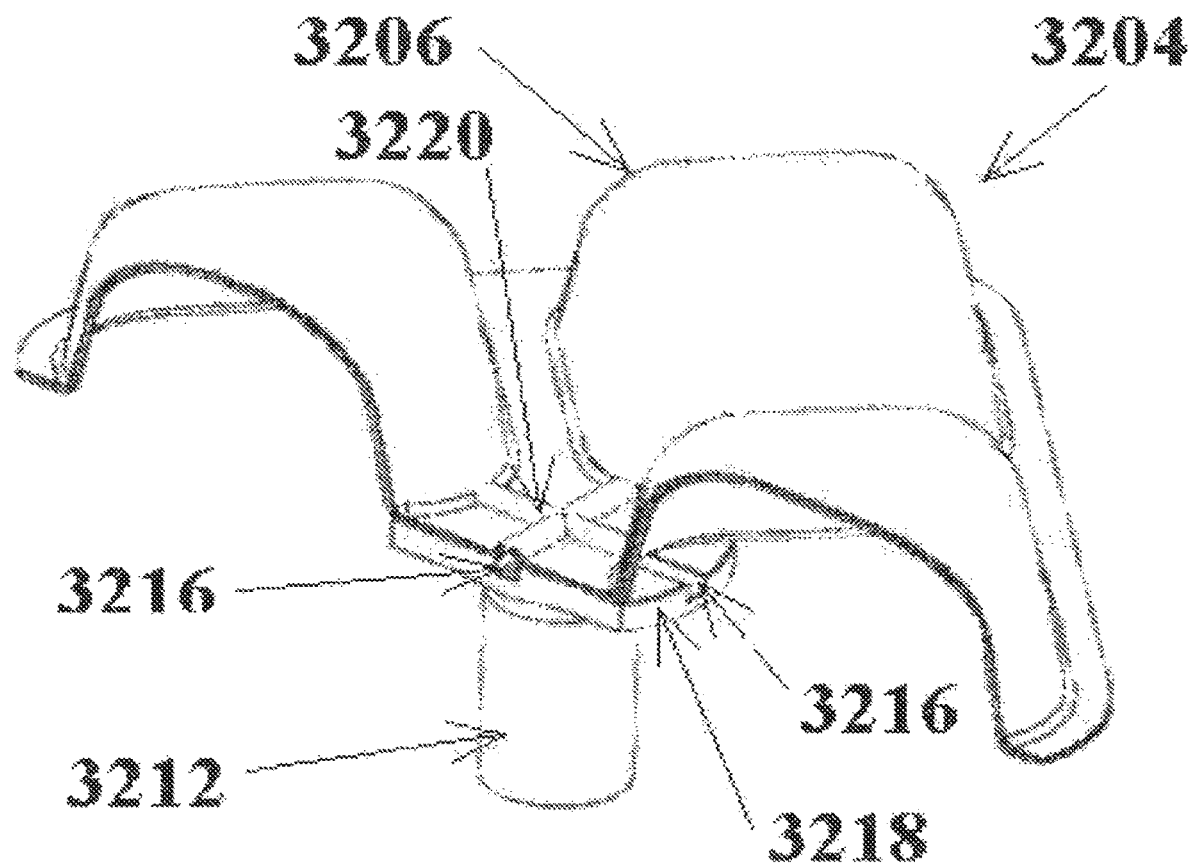
FIG. 28B is a drawing of a small bladder usable with the interface, including tubing connectors and a flange operably connected to the bladder.
Figure 29A:
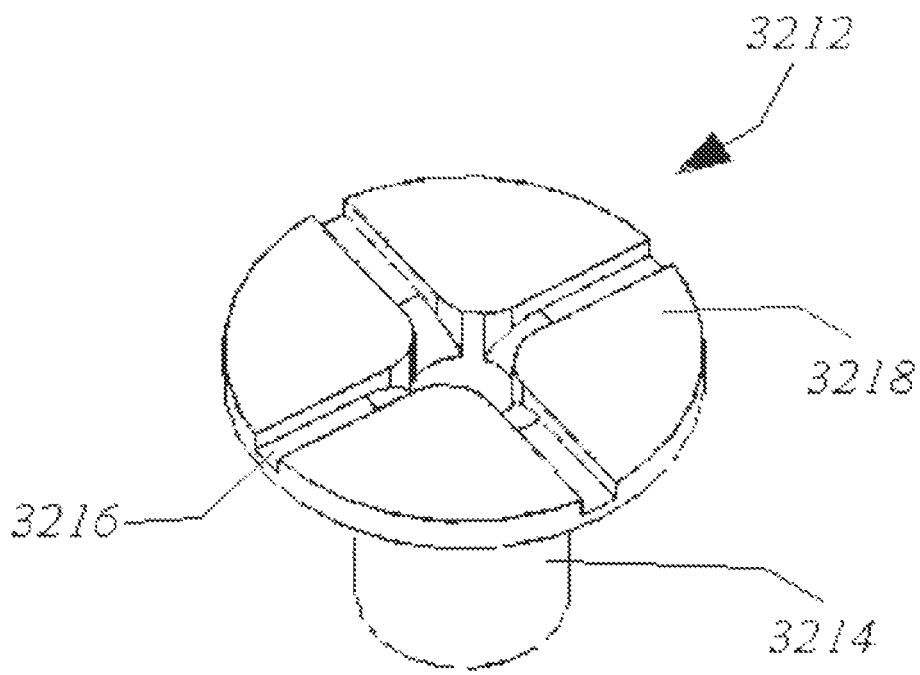
FIG. 29A is a drawing of a tubing connector usable with the interface, including additional feed/tubing, a flange operably connected to the bladder. and the tubing.
Figure 29B:
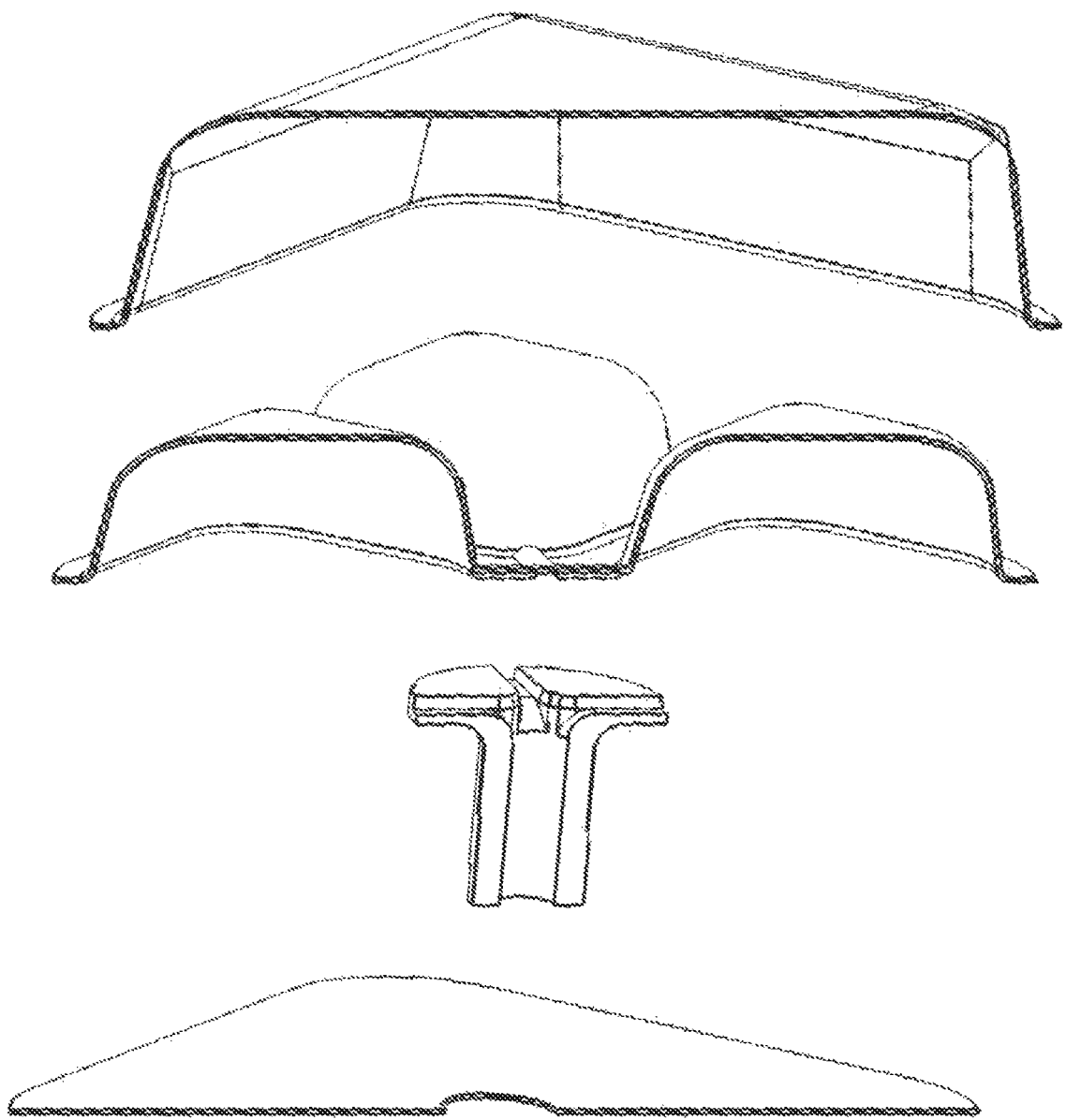
FIG. 29B is a drawing depicting further sectioned details of the integrally formed bladder assembly usable with the interface, in which the fixed volume of generally non-compressible fluid is filled with foam.
Figure 29C:
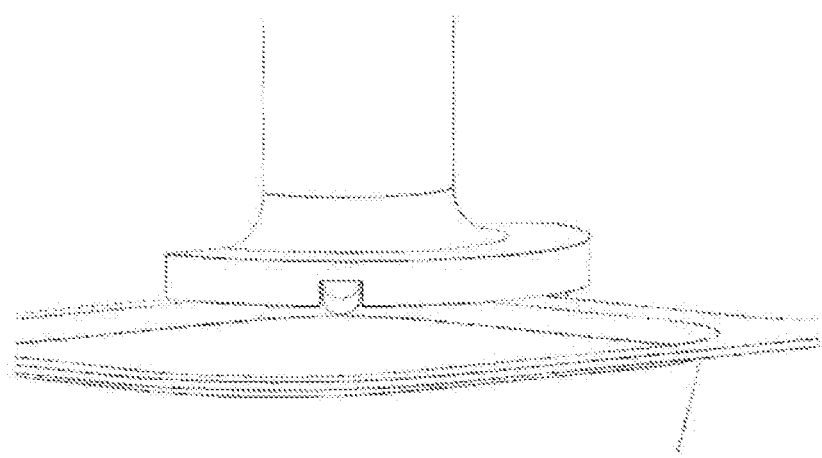
FIG. 29C is a drawing depicting further sectioned details of the integrally formed bladder assembly usable with the interface, in which the fixed volume of generally non-compressible fluid is filled with floam.
Figure 29D:
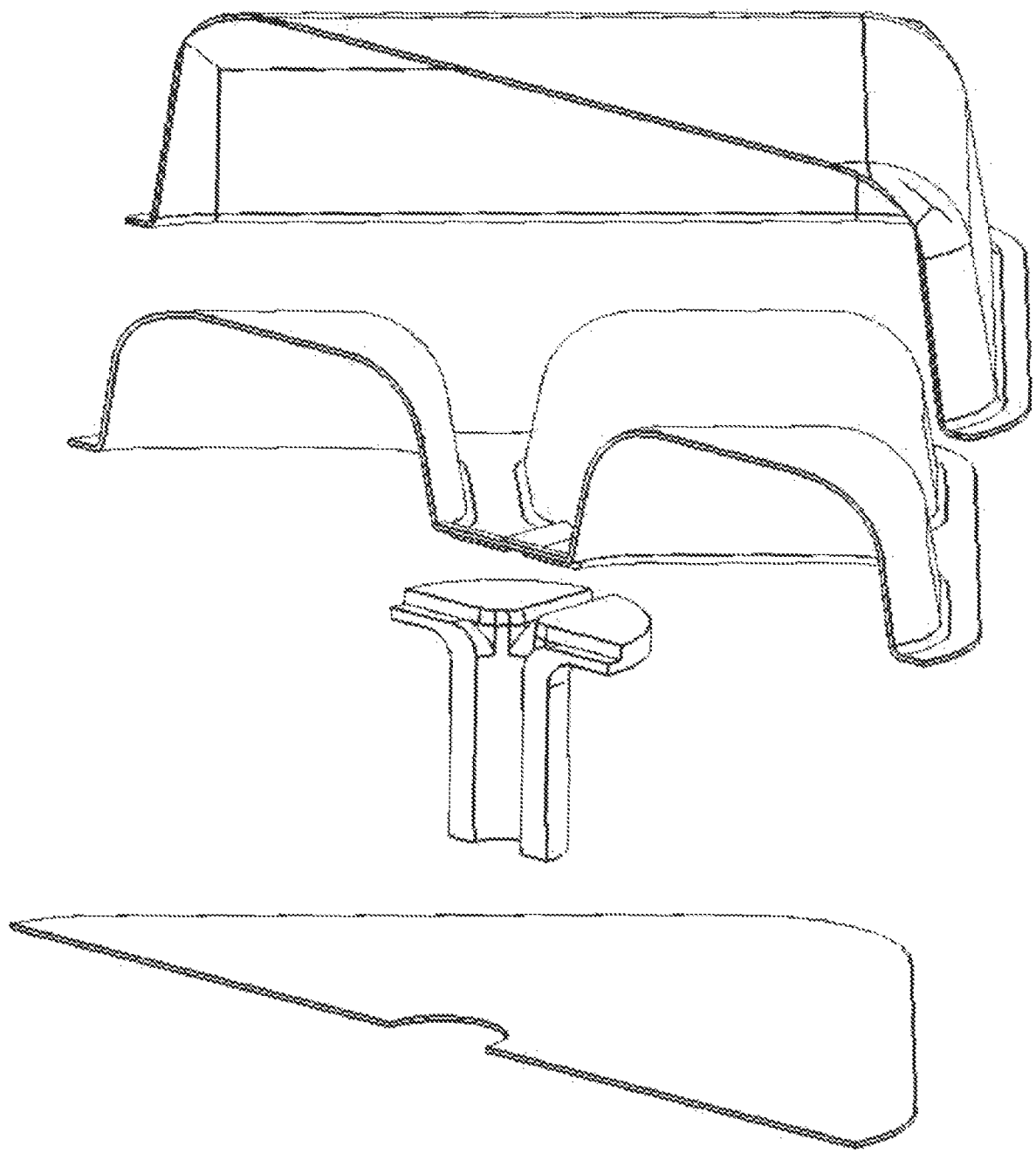
FIG. 29D is a drawing depicting further sectioned details of the integrally formed bladder assembly usable with the interface, in which the fixed volume of generally non-compressible fluid is filled with floam.
Figure 30:
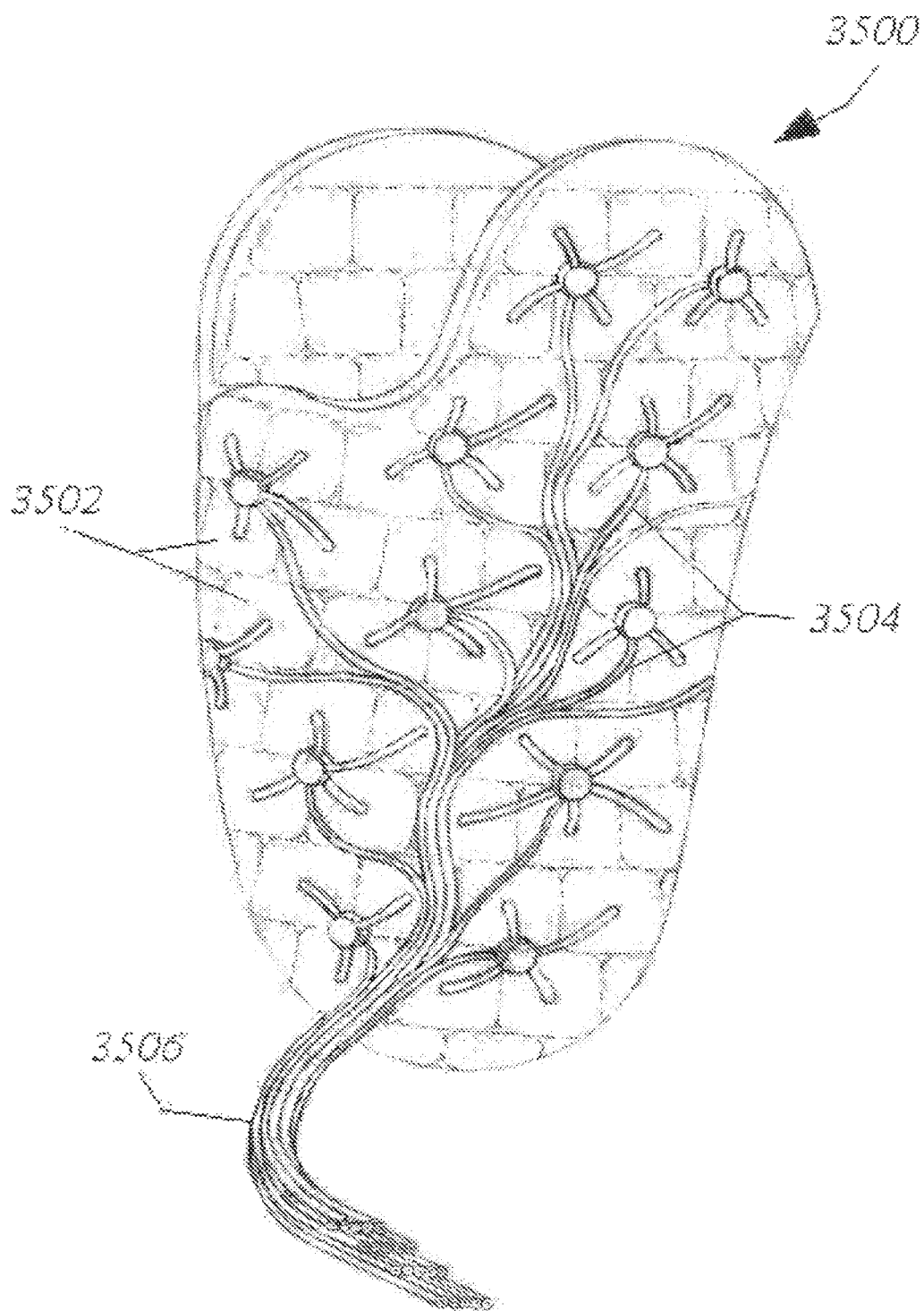
FIG. 30 is a drawing of an interface using a tube or fluid line routed from the bladder through a single hole in the socket.
Figure 32:
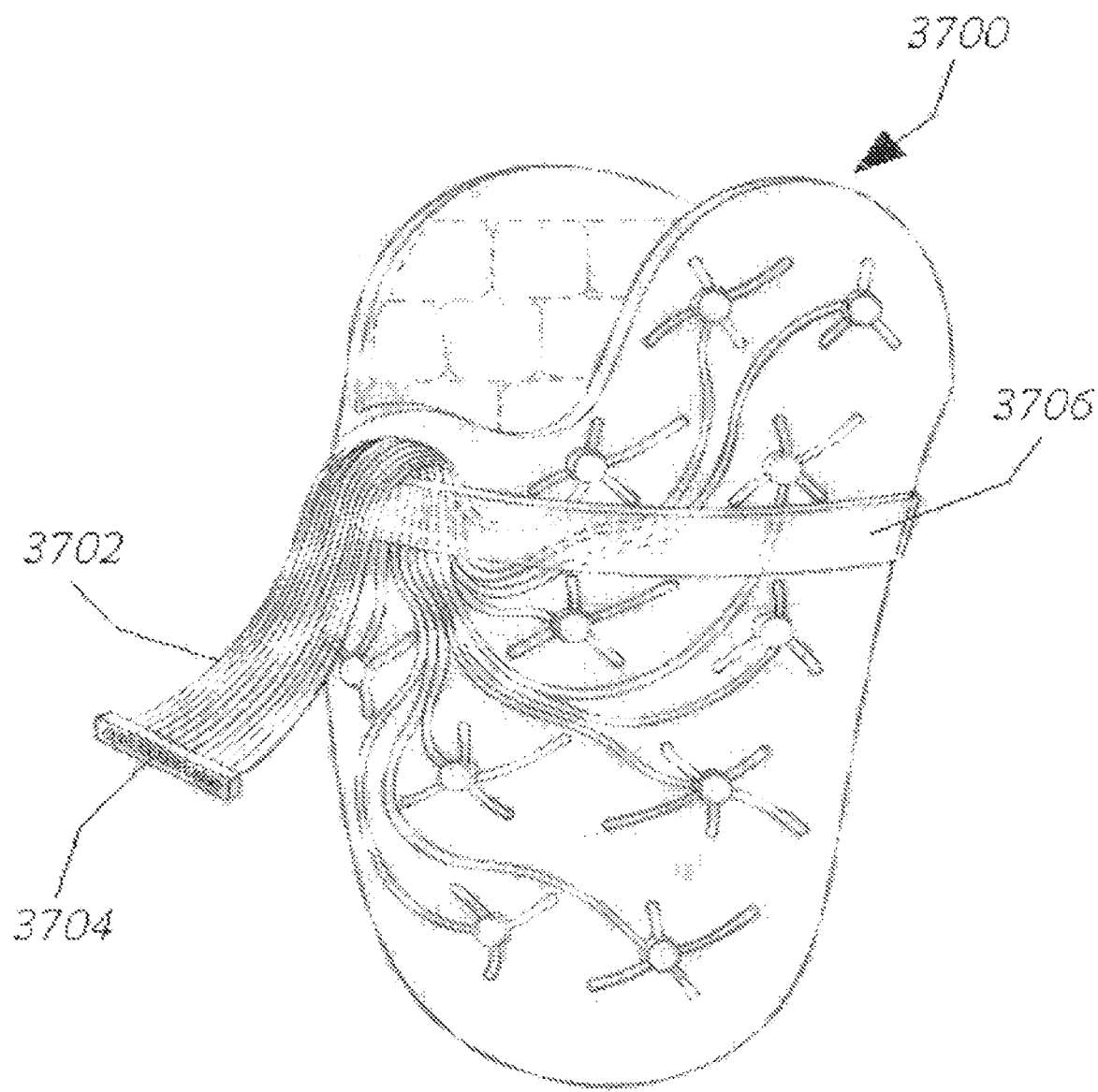
FIG. 32 is a drawing of an interface using a tube or fluid line routed from the bladder through a single hole in the socket.

Some of the other drawings show the use of "generic" size bladders (e.g., FIGS. 18. 30b, and 30c), and illustrate relatively and/or much more complicated systems for pumping oil or other fluid to adjust the volume/pressure. Some even illustrate the concept of the viscous fluid bladder having formed within it one or more adjustable elements. For example, further details of one of the many "integrally formed" bladder assemblies of the invention are shown in FIGS. 32A-C. These show various exploded views of a preferred "dual chambered" and/or multi-layered bladder assembly 3200. As mentioned above, in this and other such embodiments, the "layers" can be integrated with each other in a wide variety of arrangements. In the embodiment of FIGS. 32A-C, a "layer" of larger bladders 3202 can be provided, with one or more of those bladders 3202 having within it one or more smaller bladders 3206 (four are shown in FIGS. 32A-C). In such embodiments, the complete bladder assembly 3200 can be adjusted in numerous ways (including for example, by adjusting the amount of fluid within the smaller bladders 3206, adjusting the amount of fluid within the larger bladder 3202 (between the smaller and larger bladders), or a combination of the two). In a preferred embodiment, adjusting the volume of fluid within the smaller bladders 3206 would correspondingly adjust the volume of the larger bladder 3202 (because the smaller bladders are completely contained within the larger bladders), but the reverse would not be true (adjusting the fluid volume in a larger "covering" bladder such as bladder 3202 would not directly change the volume in the smaller bladders 3206 within it, assuming that the fluid in the smaller bladders is relatively incompressible).

Figure 31:
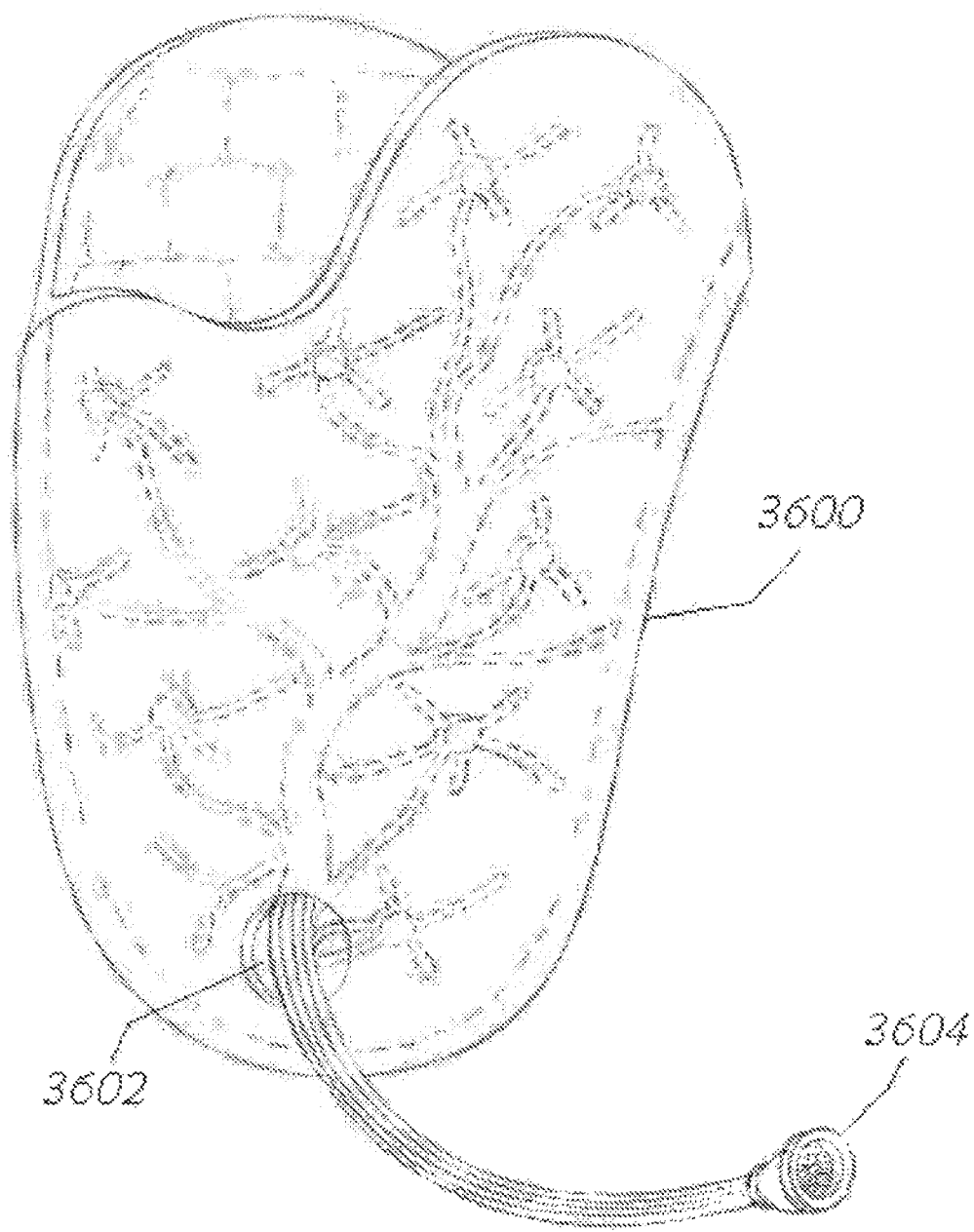
FIG. 31 is a drawing of an interface using a tube or fluid line routed from the bladder through a single hole in the socket.
Figure 33:
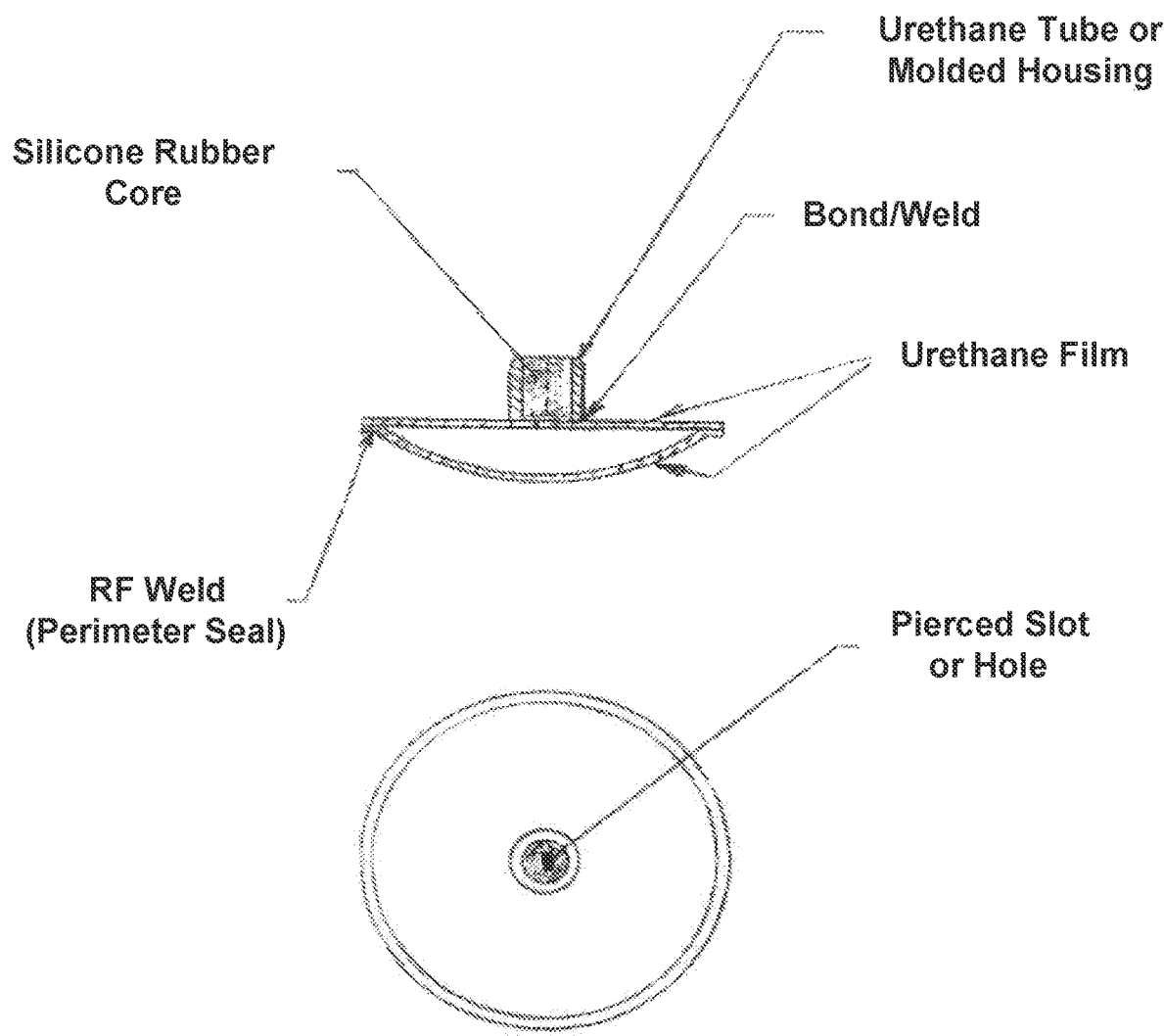
FIG. 33 is a drawing showing a self-sealing needle port usable with an interface to do one or more of fill and drain a fluid dome.

Persons of ordinary skill in the art will understand that the various elements in FIGS. 32A-C preferably are assembled and sealed together into a fluid-tight relationship such as shown in FIG. 31 and further discussed herein. A preferred relationship of two of the components 3212 and 3204 is also shown in FIGS. 33 and 33B. In one embodiment, the other elements 3202 and 3208 in FIGS. 32A and 32B are sealed around elements 3212 and 3204 (except for the stein 3214 of tubing connector 3212, which preferably protrudes through opening 3208), providing four adjustable cells 3204 (controllable via fluid pumped in or out of tubing connector 3212) within a larger cell 3202 (which preferably constitutes a sealed/non-adjustable cell, with a fixed amount of fluid in the space between it and the smaller bladders 3204). Persons of ordinary skill in the art will understand that cells 3204 are examples of a plurality of bladders interconnected with each other such that fluid can flow form one bladder to another, such as through channels 3216 in FIG. 33A.

In this embodiment, the elongated stem of tubing connector 3212 can be inserted from the inside of the socket 3000 through a selected opening 3008. Persons of ordinary skill in the art will understand that the length and other dimensions of the stem tube can be any of a wide range of convenient sizes. In this embodiment, the stem is sufficiently long to extend generally through the socket 3000, sufficiently for it to be attached to a feed line on the outside of the socket. In other embodiments, the tubing connector 3212's stem 3214 may be shorter (so that it can be connected to feed lines and/or zone lines on the interior of the socket without unduly pushing inwardly against the wearer's stump) or longer (even to the point of extending in a continuous tube all the way back to a manifold or other fluid source). Persons of ordinary skill in the art will understand that this tube tubing connector 3212 is just one of a wide range of devices by which fluid can be distributed and controlled within various embodiments of the invention.

In one embodiment, the tubing connector 3212 is injection molded from lightweight but sturdy plastic, so that it can reliably withstand the pressures and other forces to which it may be subjected and not leak or otherwise fail. Persons of ordinary skill in the art will understand that any of a wide range of suitable materials and fabrication methods may be used for the tubing connector 3212 and the other components of the various bladders and apparatus of the system.

In some embodiments, one or more tubing connectors 3212 can be positioned to extend from the inside of the socket 3000 outwardly through the tubing openings 3008. Additional feed/tubing lines can be attached in any suitable non-leaking manner to the stem 3214 of each connector 3212, and the tubing operatively connected in any suitable manner to a fluid source, such as a pump, reservoir, or manifold, or even just to other bladders/zones within the prosthesis. As mentioned elsewhere herein, the selected arrangement and valves, tees, connectors, and other "plumbing" within the fluid distribution system can provide great flexibility in the control of fluid to and from the bladders (or selected bladders). In such embodiments, the flange 3218 is then operatively connected (again, in a non-leaking manner) to one or more bladders and/or zones of bladders within the socket 3000. The tubing connectors 3212 can be temporarily or permanently affixed to the socket 3000 (by adhesive, welding, or other suitable method), or can be "loose" and free to slide in and out of the holes 3008.

Among many other embodiments, the tubing connector or connectors 3212 can be assembled with a bladder or bladders prior to being assembled into a socket. As indicated above, a plurality of such bladders (with or without tubing connectors or similar fluid connectivity) can be assembled together into one or more liner elements, which can be placed into a desired relationship with a socket, around the wearer's stump, at a particular location on a wearer's stump, etc.

As discussed elsewhere, the individual bladders or cells can be fabricated in a wide range of suitable sizes, shapes, and arrangements, and from any of a wide range of suitable materials. One of the many ways to construct embodiments such as illustrated in FIGS. 32A-C is to melt or weld (or glue, or use any suitable means to seal) various layers of materials together to form/seal the desired bladders, including placing them into a form to be adjustable or not, as desired for the specific application. A first layer of material 3208 preferably is at least as large as a single cell assembly. Persons of ordinary skill in the art will understand that the layer 3208 can alternatively be sufficiently large (compared to the cell/bladder size) to include a plurality of cells and/or zones on it. As mentioned above, a plurality of such sheets and/or individual cells may be affixed to each other (along their edges 3210 or otherwise) to themselves form a larger liner assembly or other useful construction. Persons of ordinary skill in the art will understand that other techniques can be used to form the various parts of the bladders, including vacuum-forming, blow-molding, or the like. Among other things, the molds used in such processes can enable a precisely curved configuration and other desirable shaping for the packet/bladder/etc.

Openings can be provided in the sheet 3208 at appropriate locations to permit insertion of one or more tubing connectors 3212. The tubing connector (if present) is then overlaid with an inner pod 3204 of one or more cells (four cells are shown in FIG. 32B, for example). A larger bladder shell 3202 can then be placed over the pod 3204, so that the edges of those elements can be sealed in some suitable manner to form the fluid bladders. If one or more of the bladders is to be adjustable, a fluid path (such as described below) can be provided to permit flow of fluid into and/or out of the particular cell or cells.

In the embodiment of FIG. 32B, for example, the larger shell preferably includes a flange extending outwardly from its lower edge. That flange is configured to overlay and contact a similar outer flange element on the pod 3204, which in turn can be placed against the sheet element 3208 in an operative relationship with the tubing connector 3212 and the associated hole through the sheet 3208. To enable the desired adjustability of embodiments such as assembly 3200 (FIG. 32B), the various components 3202, 3204, and 3208 can then be sealed, glued, welded, or otherwise connected to each other at their edges, with a sufficiently strong seal to withstand anticipated forces and fluid pressures without leaking. To provide the desired control of fluid flow into and out of the chambers 3204, the central webbing between each of those cells must likewise be operatively sealed to the material underlying it (contacting portions of the sheet 3208 and/or portions of the flange on tubing connector 3212. Connector 3212 may also be welded or otherwise attached to the sheet 3208. Persons of ordinary skill in the art will understand that the particular order of these assembly steps can be any convenient/suitable/economical order. Thus, for example, the tubing connector flange 3218 can be welded to the bottom layer 3208, then the pod 3204 can be welded at its edges (and completely around the periphery of each individual cell in the pod 3204), and finally the outer shell 3202 can be filled with a desired fluid, placed over the pod 3204, and welded at its edges (again, preferably ensuring that no air or other compressible fluid remains between elements 3202 and 3204). In the embodiment of FIG. 32B, that space is not adjustable, but persons of ordinary skill in the art will understand that other embodiments can include means to adjust the fluid volume within that space, via further or different tubing connectors, fill lines, etc.

For ease and/or economy of fabrication (or for other reasons), not only can the base sheet 3208 be larger than a single cell 3200, but the other elements 3202 and 3204 can likewise extend laterally. If those other materials are provided in a repeating pattern, sheets and/or strips or other shapes of multiple bladders can be fabricated simultaneously and/or continuously, by sealing a plurality of such bladders in a single press or in a continuous feed into a welding/sealing device. Persons of ordinary skill in the art will understand that any suitable system may be used to fabricate the cells and other components of the invention.

Figure 34:
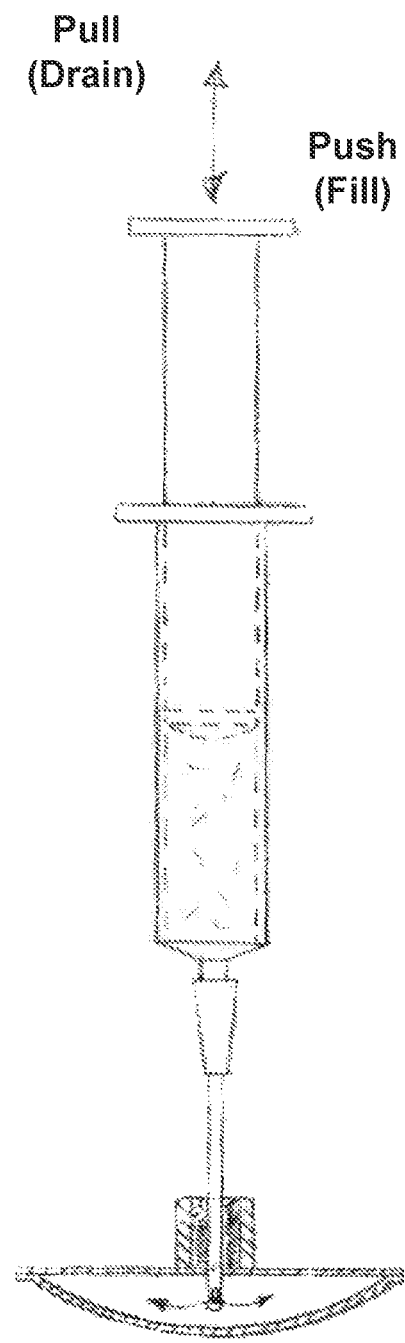
FIG. 34 is a drawing showing a self-sealing needle port usable with an interface to do one or more of fill and drain a fluid dome.

As indicated above, for embodiments in which the space between the pod 3204 and the shell 3202 is filled with a fixed amount of fluid and not adjustable (i.e., a fixed volume of fluid is to be maintained in that space), that fluid preferably is injected or otherwise placed into that space prior to the sealing of the cell, and any air or similarly relatively compressible fluid/gas is extracted from the cell prior to that sealing. Persons of ordinary skill in the art will understand that such embodiments thereby can ensure that the "fixed volume" of generally non-compressible fluid will not be displaced from the cell during loading conditions, and thus can help ensure that the cell does not "bottom out" under conditions of stress or use. As indicated above, that "fixed volume" can be filled with the FLOAM® or other putty-like, cushioning, relatively fluid material. FIGS. 34A-34C show further sectioned details and view of this type of embodiment.

Further aspects of the flexibility and customizable nature of various embodiments of the invention are illustrated in FIG. 30c, 31, 31a, and 31b. FIG. 31 is a sectioned view of the socket 3000 and liner 3012 assembly of FIG. 30C (taken along line 31-31 of FIG. 30C). Although holes 3008 are formed in the socket wall, the putty packets 3014 inside are not adjustable, so no tubes are positioned in those holes. FIG. 31a also illustrates embodiments in which valves (similar to the valves on basketballs or other sports balls) fill the holes 3008 and allow adjustment of the bladders 3014. FIG. 31a is similar, but shows an embodiment having a radially innermost internal skin barrier/sheath 3010, as well as one of the many relatively more complicated "multi-chamber" bladder embodiments discussed below. Among other things, FIG. 31 reveals various layers, such as a hard socket wall 3000, cells/bladders 3002 (which may be any of a wide range of designs, including for example the "dual chambered" cells described here (FLOAM®/putty on top of adjustable oil/other domes, all within a single cell packet), in which one or more additional smaller bladders 3018 are located in the area 3004 within the bladder 3002), and an internal barrier/sheath 3010. FIG. 31 also illustrates a preferred positioning of the openings 3008 through the socket 3000, to facilitate a preferred method and apparatus for adjustment of the bladders/zones that are adjacent each respective opening 3008.

In the cross-section illustrated in FIG. 31B, an interior liner 3010 is again shown, along with many other elements similar to those in FIGS. 31 and 31A. In addition, however, FIG. 31B also illustrates a further layer of bladders 3024 positioned radially inwardly from the socket (toward the wearer's residual limb). As with the other bladders, these radially-further-inward ones may be adjustable or not, and may otherwise be selectively sized, shaped, positioned, filled, and otherwise configured to provide a desired feel and function to the wearer.

In other words, depending on the needs of a particular wearer, a wide range of cell/bladder configurations can be used to practice the methods and apparatus of the invention. These configurations range from relatively "simple" embodiments (such as a single, non-adjustable layer of bladders 3002 that do not have fill lines inserted through socket openings 3008) to more complicated embodiments (such as the integrated cell/bladder embodiments shown in FIGS. 32A-C and discussed further below, in which one or more additional smaller bladders 3018 can be positioned within the interior 3004 of one or more of the bladders 3002, and/or the multiple "separate" bladder layers shown in FIG. 31).

For the purpose of summarizing the invention, certain objects and advantages have been described herein. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The apparatus and methods of the invention have been described with some particularity, but the specific designs, constructions, and steps disclosed are not to be taken as delimiting of the invention. A wide range of modifications and alternative structures and steps for practicing the invention will make themselves apparent to those of ordinary skill in the art, all of which will not depart from the essence of the invention, and all such changes and modifications are intended to be encompassed within the claims.

The inventions claimed include the following:

1. Apparatus for cushioning between a prosthetic socket and an amputee's residual limb, including:
    a plurality of non-adjustable packets configured when assembled to form a liner between a socket and an amputee's residual limb, wherein the packets contain a putty,
    a plurality of adjustable bladders forming a second liner configured to cover at least a portion of the contact area between a socket and an amputee's residual limb, said bladders having within incompressible fluid, and
    means for selectively increasing and/or decreasing the volume of incompressible fluid in said plurality of adjustable bladders.

* * * * *